US007314715B2

(12) United States Patent
Cochran et al.

(10) Patent No.: US 7,314,715 B2
(45) Date of Patent: Jan. 1, 2008

(54) RECOMBINANT AVIAN HERPESVIRUS USEFUL IN VACCINE PRODUCTION

(75) Inventors: Mark D. Cochran, Carlsbad, CA (US); Stephanie M. Cook, Omaha, NE (US); Martha A. Wild, San Diego, CA (US)

(73) Assignee: Schering-Plough Animal Health Corporation, Summit, NJ (US)

( * ) Notice: Subject to any disclaimer, the term of this patent is extended or adjusted under 35 U.S.C. 154(b) by 398 days.

(21) Appl. No.: 11/126,465

(22) Filed: May 11, 2005

(65) Prior Publication Data

US 2005/0202045 A1  Sep. 15, 2005

Related U.S. Application Data

(63) Continuation of application No. 09/881,457, filed on Jun. 14, 2001, now Pat. No. 6,913,751.

(51) Int. Cl.
*C12Q 1/68* (2006.01)
(52) U.S. Cl. .......................................... 435/6; 435/69.1
(58) Field of Classification Search .................... 435/6, 435/69.1
See application file for complete search history.

(56) References Cited

U.S. PATENT DOCUMENTS

| 5,138,033 | A | 8/1992 | Velicer et al. |
| 5,187,087 | A | 2/1993 | Sondermeijer et al. |
| 5,231,023 | A | 7/1993 | Morgan |
| 5,252,716 | A | 10/1993 | Velicer et al. |
| 5,283,191 | A | 2/1994 | Morgan et al. |
| 5,470,734 | A | 11/1995 | Sondermeijer et al. |
| 5,506,128 | A | 4/1996 | Cochran et al. |
| 5,686,287 | A | 11/1997 | Baxendale |
| 5,690,939 | A | 11/1997 | Morgan et al. |
| 5,763,269 | A | 6/1998 | Cochran et al. |
| 5,830,745 | A | 11/1998 | Hock et al. ............... 435/235.1 |
| 5,834,305 | A | 11/1998 | Cochran et al. |
| 5,866,697 | A | 2/1999 | Velicer et al. |
| 5,928,648 | A | 7/1999 | Cochran |
| 5,961,982 | A | 10/1999 | Cochran |
| 5,965,138 | A | 10/1999 | Cochran et al. ......... 424/199.1 |
| 5,976,787 | A | 11/1999 | Velicer et al. |
| 6,051,404 | A | 4/2000 | Morgan et al. |
| 6,087,127 | A | 7/2000 | Velicer et al. |
| 6,121,043 | A | 9/2000 | Cochran et al. ......... 435/320.1 |
| 6,153,199 | A | 11/2000 | Audonnet et al. ....... 424/199.1 |
| 6,183,753 | B1 | 2/2001 | Cochran et al. |

FOREIGN PATENT DOCUMENTS

| EP | 0 486 106 A2 | 5/1992 |
| EP | 0 473 210 B1 | 4/1994 |
| EP | 0 431 668 B1 | 2/1995 |
| EP | 0 423 869 B1 | 7/1995 |
| EP | 0 513 921 B1 | 8/1995 |
| WO | WO 87/04463 | 7/1987 |
| WO | WO 92/03547 | 3/1992 |
| WO | WO 00/61736 | 10/2000 |
| WO | WO 02/36617 A2 | 5/2002 |

OTHER PUBLICATIONS

Afonso, C.L. et al., 2001, The genome of turkey herpesvirus, *J. Virol.*, 75(2):971-978.
Afonso, C.L. et al., 2001, Genbank accession No. AF291866.
Brunovskis, P. et al., 1995, The Marek's disease virus (MDV) unique short region: Alphaherpesvirus homologus, fowlpox virus-homologus, and MDV-specific genes, *Virol.*, 206:324-338.
Brunovskis, P. et al., 1995, Genbank accession No. L22174.
Buckmaster, A.E. et al., 1988, Gene sequence and mapping data from Marek's disease virus and herpesvirus of turkeys: Implications for herpesvirus classification, *J. Gen. Virol.*, 69:2033-2042.
Cantello, J.L. et al., 1991, Isolation of a Marek's disease virus (MDV) recombinant containing the *lacZ* gene of *Escherichia coli* stably inserted within the (MDV) US2 gene, *J. Virol.*, 65(3):1584-1588.
Cochran, M.D. and Macdonald, R.D., 1999, Genbank accession No. AR068186.
Cronenberg, A.M. et al., 1999, Vaccination of broilers with HVT expressing an *Eimeria acervulina* antigen improves performance after challenge with *Eimeria*, *Acta Virologica*, 43:192-197.
Darteil, R. et al., 1995, Herpesvirus of turkey recombinant viruses expressing infectious bursal disease virus (IBDV) VP2 immunogen induce protection against an IBDV virulent challenge in chickens, *Virol.*, 211:481-490.
Gubler, V. et al., 1983, A simple and very efficient method for generating cDNA libraries, *Gene*, 25:263-269.
Hanahan, D., 1983, Studies on transformation of *Escherichia coli* with plasmids, *J. Mol. Biol.*, 166:557-580.
Hirai, K. et al., 2001, Polyvalent recombinant Marek's disease virus vaccine against poultry diseases, *Curr. Top. Micro. and Immunol.*, 255:261-287.
Marshall, D.R. et al., 1993, Selection of Marek's disease virus recombinants expressing the *Escherichia coli* gpt gene, *Virol.*, 195:638-648.
McGeoch, D.J. et al., 1988, The complete DNA sequence of the long unique region in the genome of herpes simplex virus type 1, *J. Gen. Virol.*, 69:1531-1574.
McGeoch, D.J. et al., 1999, Genbank accession No. D10879.
Morgan, R.W. et al., 1993, Efficacy in chickens of a herpesvirus of turkeys recombinant vaccine containing the fusion gene of Newcastle disease virus: Onset of protection and effect of maternal antibodies, *Avian Diseases*, 37:1032-1040.
Parcells, M.S. et al., 1994, Characterization of a Marek's disease virus mutant containing a *lacZ* insertion in the US6 (gD) homologue gene, *Virus Genes*, 9(1):5-13.
Ross, L.J.N., 1998, Recombinant vaccines against Marek's disease, *Avian Pathol.*, 27:S65-S73.

(Continued)

Primary Examiner—Ali R. Salimi

(57) ABSTRACT

The present invention provides a novel avian herpesvirus (NAHV) vector and recombinant vaccines made therefrom that are useful to immunize avian species against Marek's disease, infectious laryngotracheitis and Newcastle disease. Methods of immunizing an avian species against Marek's disease, infectious laryngotracheitis and Newcastle disease are also provided.

3 Claims, 2 Drawing Sheets

OTHER PUBLICATIONS

Sakaguchi, M. et al., 1994, Construction of recombinant Marek's disease virus type 1 (MDV1) expressing the *Escherichia coli lacZ* gene as a possible live vaccine vector: The US 10 gene of MV1 as a stable Insertion site, *Vaccine*, 12(10):953-957.

Sakaguchi, M. et al., 1998, Protection of chickens with or without maternal antibodies against both Marek's and Newcastle diseases by one-time vaccination with recombinant vaccine of Marek's disease virus type 1, *Vaccine*, 16(5):472-479.

Scharf, S.J., 1990, PCR Protocols: A Guide to Methods and Applications, In: Cloning with PCR, New York: Academic Press, Inc., pp. 84-91.

Sondermeijer, P.J.A. et al., 1993, Avian herpesvirus as a live viral vector for the expression of heterologous antigens, *Vaccine*, 11(3):349-358.

Sonoda, K. et al., 2000, Development of an Effective Polyvalent Vaccine against both Marek's and Newcastle Diseases Based on Recombinant Marek's Disease Virus Type 1 in Commercial Chickens with Maternal Antibodies, *Journal of Virology*, vol. 74, No. 7, pp. 3217-3226.

Van Zijl, M. et al., 1988, Regeneration of Herpesvirus from Molecularly Cloned Subgenomic Fragments, Journal of Virology, vol. 62, No. 6, pp. 2191-2195.

Wild, M.A. et al., 1996, A Genomic Map of Infectious Layngotracheitis Virus and the Sequence and Organization of Genes Present in the Unique Short and Flanking Regions, *Virus Genes* 12:2, pp. 107-116.

Wild, M.A. et al., 1996, Genbank accession No. U28832.

Kingham, et al., Journal of General Virology, May 2001, vol. 82, 1123-1135.

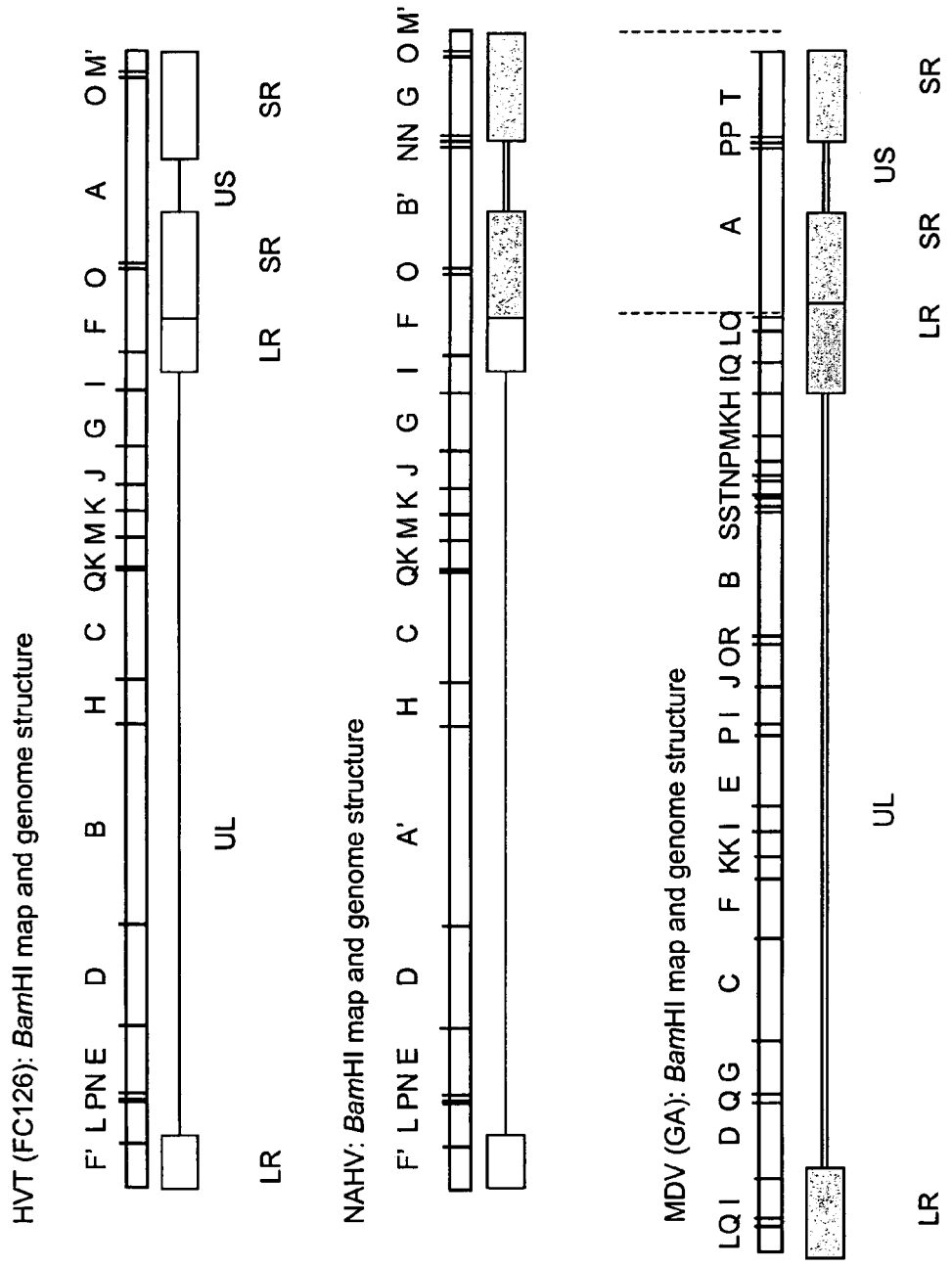
Figure 1: Comparison of HVT, NAHV and MDV BamHI maps

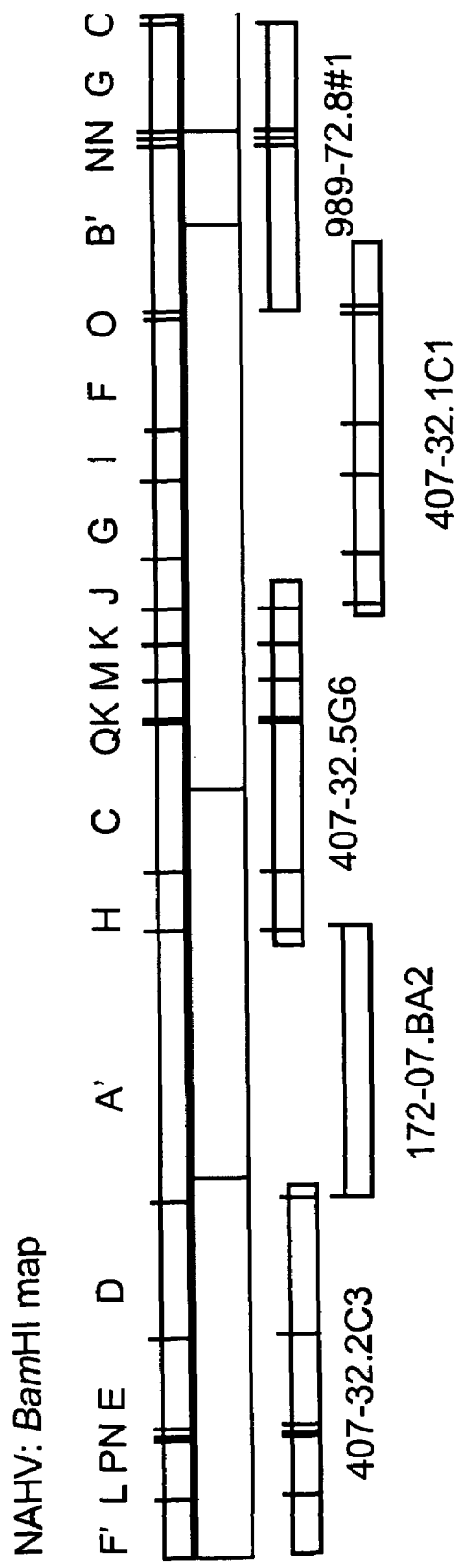
Figure 2: NAHV BamHI map and position of cosmids used in NAHV construction

SEQUENCE LISTING

<160> NUMBER OF SEQ ID NOS: 5

<210> SEQ ID NO 1
<211> LENGTH: 3570
<212> TYPE: DNA
<213> ORGANISM: Newcastle disease virus
<220> FEATURE:
<221> NAME/KEY: CDS
<222> LOCATION: (1194)..(2888)
<223> OTHER INFORMATION: NDV Fusion Protein
<220> FEATURE:
<221> NAME/KEY: misc_feature
<222> LOCATION: (1355)
<223> OTHER INFORMATION: n = any nucleotide

<400> SEQUENCE: 1

```
gtacgttaat taacccggga agcttgcatg cctgcagtga ataataaaat gtgtgtttgt      60
ccgaaatacg cgttttgaga tttctgtcgc cgactaaatt catgtcgcgc gatagtggtg     120
tttatcgccg atagagatgg cgatattgga aaaatcgata tttgaaaata tggcatattg     180
aaaatgtcgc cgatgtgagt ttctgtgtaa ctgatatctg gcgatagcgc ttatatcgtt     240
tacgggggat ggcgatagac gactttggcg acttgggcga ttctgtgtgt cgcaaatatc     300
gcagtttcga tataggtgac agacgatatg aggctatatc gccgatagag gcgacatcaa     360
gctggcacat ggccaatgca tatcgatcta tacattgaat caatattggc aattagccat     420
attagtcatt ggttatatag cataaatcaa tattggctat tggccattgc atacgttgta     480
tctatatcat aatatgtaca tttatattgg ctcatgtcca atatgaccgc catgttgaca     540
ttgattattg actagttatt aatagtaatc aattacgggg tcattagttc atagcccata     600
tatggagttc cgcgttacat aacttacggt aaatggcccg cctggctgac cgcccaacga     660
ccccccgccca ttgacgtcaa taatgacgta tgttcccata gtaacgccaa tagggacttt     720
ccattgacgt caatgggtgg agtatttacg gtaaactgcc cacttggcag tacatcaagt     780
gtatcatatg ccaagtccgc ccctattga cgtcaatgac ggtaaatggc ccgcctggca     840
ttatgcccag tacatgacct tacgggactt tcctacttgg cagtacatct acgtattagt     900
catcgctatt accatggtga tgcggttttg gcagtacacc aatgggcgtg gatagcggtt     960
tgactcacgg ggatttccaa gtctccaccc cattgacgtc aatgggagtt tgttttggca    1020
ccaaaatcaa cgggactttc caaaatgtcg taataacccc gccccgttga cgcaaatggg    1080
cggtaggcgt gtacggtggg aggtctatat aagcagagct cgtttagtga accgtcagat    1140
cgcctggaga cgccatccac gctgttttga cctccataga agacaccggg acc atg       1196
                                                              Met
                                                                1 gat cga tcc cgg ttg gcg ccc tcc agg tgc agg atg ggc tcc aga cct       1244
Asp Arg Ser Arg Leu Ala Pro Ser Arg Cys Arg Met Gly Ser Arg Pro
         5                  10                  15 tct acc aag aac cca gca cct atg atg ctg act atc cgg gtc gcg ctg       1292
Ser Thr Lys Asn Pro Ala Pro Met Met Leu Thr Ile Arg Val Ala Leu
     20                  25                  30 gta ctg agt tgc atc tgt ccg gca aac tcc att gat ggc agg cct ctt       1340
Val Leu Ser Cys Ile Cys Pro Ala Asn Ser Ile Asp Gly Arg Pro Leu
 35                  40                  45 gca gct gca gga ctn tgg tta cag gag aca aag caa tca aca tat aca       1388
Ala Ala Ala Gly Xaa Trp Leu Gln Glu Thr Lys Gln Ser Thr Tyr Thr
 50                  55                  60                  65
```

```
cct cat ccc aga cag gtc aat cat att aag ctc ctc ccg aat ctg cca    1436
Pro His Pro Arg Gln Val Asn His Ile Lys Leu Leu Pro Asn Leu Pro
             70                  75                  80 aag gat aag gag gca tgt gcg aaa gcc ccc ttg gat gca tac aac agg    1484
Lys Asp Lys Glu Ala Cys Ala Lys Ala Pro Leu Asp Ala Tyr Asn Arg
         85                  90                  95 aca ttg acc act ttg ctc acc ccc ctt ggt gac tct atc cgt agg ata    1532
Thr Leu Thr Thr Leu Leu Thr Pro Leu Gly Asp Ser Ile Arg Arg Ile
     100                 105                 110 caa gag tct gtg act aca tct gga ggg ggg aga cag ggg cgc ctt ata    1580
Gln Glu Ser Val Thr Thr Ser Gly Gly Gly Arg Gln Gly Arg Leu Ile
 115                 120                 125 ggc gcc att att ggc ggt gtg gct ctt ggg gtt gca act gcc gca caa    1628
Gly Ala Ile Ile Gly Gly Val Ala Leu Gly Val Ala Thr Ala Ala Gln
130                 135                 140                 145 ata aca gcg gcc gca gct ctg ata caa gcc aaa caa aat gct gcc aac    1676
Ile Thr Ala Ala Ala Ala Leu Ile Gln Ala Lys Gln Asn Ala Ala Asn
             150                 155                 160 atc ctc cga ctt aaa gag agc att gcc gca acc aat gag gct gtg cat    1724
Ile Leu Arg Leu Lys Glu Ser Ile Ala Ala Thr Asn Glu Ala Val His
         165                 170                 175 gag gtc act gac gga tta tcg caa cta gca gtg gca gtt ggg aag atg    1772
Glu Val Thr Asp Gly Leu Ser Gln Leu Ala Val Ala Val Gly Lys Met
     180                 185                 190 cag cag ttc gtt aat gac caa ttt aat aaa aca gct cag gaa tta gac    1820
Gln Gln Phe Val Asn Asp Gln Phe Asn Lys Thr Ala Gln Glu Leu Asp
 195                 200                 205 tgc atc aaa att gca cag caa gtt ggt gta gag ctc aac ctg tac cta    1868
Cys Ile Lys Ile Ala Gln Gln Val Gly Val Glu Leu Asn Leu Tyr Leu
210                 215                 220                 225 acc gaa tcg act aca gta ttc gga cca caa atc act tca cct gcc tta    1916
Thr Glu Ser Thr Thr Val Phe Gly Pro Gln Ile Thr Ser Pro Ala Leu
             230                 235                 240 aac aag ctg act att cag gca ctt tac aat cta gct ggt ggg aat atg    1964
Asn Lys Leu Thr Ile Gln Ala Leu Tyr Asn Leu Ala Gly Gly Asn Met
         245                 250                 255 gat tac tta ttg act aag tta ggt ata ggg aac aat caa ctc agc tca    2012
Asp Tyr Leu Leu Thr Lys Leu Gly Ile Gly Asn Asn Gln Leu Ser Ser
     260                 265                 270 tta atc ggt agc ggc tta atc acc ggt aac cct att cta tac gac tca    2060
Leu Ile Gly Ser Gly Leu Ile Thr Gly Asn Pro Ile Leu Tyr Asp Ser
 275                 280                 285 cag act caa ctc ttg ggt ata cag gta act cta cct tca gtc ggg aac    2108
Gln Thr Gln Leu Leu Gly Ile Gln Val Thr Leu Pro Ser Val Gly Asn
290                 295                 300                 305 cta aat aat atg cgt gcc acc tac ttg gaa acc tta tcc gta agc aca    2156
Leu Asn Asn Met Arg Ala Thr Tyr Leu Glu Thr Leu Ser Val Ser Thr
             310                 315                 320 acc agg gga ttt gcc tcg gca ctt gtc cca aaa gtg gtg aca cgg gtc    2204
Thr Arg Gly Phe Ala Ser Ala Leu Val Pro Lys Val Val Thr Arg Val
         325                 330                 335 ggt tct gtg ata gaa gaa ctt gac acc tca tac tgt ata gaa act gac    2252
Gly Ser Val Ile Glu Glu Leu Asp Thr Ser Tyr Cys Ile Glu Thr Asp
     340                 345                 350 tta gat tta tat tgt aca aga ata gta acg ttc cct atg tcc cct ggt    2300
Leu Asp Leu Tyr Cys Thr Arg Ile Val Thr Phe Pro Met Ser Pro Gly
 355                 360                 365 att tac tcc tgc ttg agc ggc aat aca tcg gcc tgt atg tac tca aag    2348
Ile Tyr Ser Cys Leu Ser Gly Asn Thr Ser Ala Cys Met Tyr Ser Lys
370                 375                 380                 385
```

```
acc gaa ggc gca ctt act aca cca tat atg act atc aaa ggc tca gtc      2396
Thr Glu Gly Ala Leu Thr Thr Pro Tyr Met Thr Ile Lys Gly Ser Val
                390                 395                 400 atc gct aac tgc aag atg aca aca tgt aga tgt gta aac ccc ccg ggt      2444
Ile Ala Asn Cys Lys Met Thr Thr Cys Arg Cys Val Asn Pro Pro Gly
            405                 410                 415 atc ata tcg caa aac tat gga gaa gcc gtg tct cta ata gat aaa caa      2492
Ile Ile Ser Gln Asn Tyr Gly Glu Ala Val Ser Leu Ile Asp Lys Gln
        420                 425                 430 tca tgc aat gtt tta tcc tta ggc ggg ata act tta agg ctc agt ggg      2540
Ser Cys Asn Val Leu Ser Leu Gly Gly Ile Thr Leu Arg Leu Ser Gly
    435                 440                 445 gaa ttc gat gta act tat cag aag aat atc tca ata caa gat tct caa      2588
Glu Phe Asp Val Thr Tyr Gln Lys Asn Ile Ser Ile Gln Asp Ser Gln
450                 455                 460                 465 gta ata ata aca ggc aat ctt gat atc tca act gag ctt ggg aat gtc      2636
Val Ile Ile Thr Gly Asn Leu Asp Ile Ser Thr Glu Leu Gly Asn Val
                470                 475                 480 aac aac tcg atc agt aat gcc ttg aat aag tta gag gaa agc aac aga      2684
Asn Asn Ser Ile Ser Asn Ala Leu Asn Lys Leu Glu Glu Ser Asn Arg
            485                 490                 495 aaa cta gac aaa gtc aat gtc aaa ctg acc agc aca tct gct ctc att      2732
Lys Leu Asp Lys Val Asn Val Lys Leu Thr Ser Thr Ser Ala Leu Ile
        500                 505                 510 acc tat atc gtt ttg act atc ata tct ctt gtt ttt ggt ata ctt agc      2780
Thr Tyr Ile Val Leu Thr Ile Ile Ser Leu Val Phe Gly Ile Leu Ser
    515                 520                 525 ctg att cta gca tgc tac cta atg tac aag caa aag gcg caa caa aag      2828
Leu Ile Leu Ala Cys Tyr Leu Met Tyr Lys Gln Lys Ala Gln Gln Lys
530                 535                 540                 545 acc tta tta tgg ctt ggg aat aat acc cta gat cag atg aga gcc act      2876
Thr Leu Leu Trp Leu Gly Asn Asn Thr Leu Asp Gln Met Arg Ala Thr
                550                 555                 560 aca aaa atg tga acacagatga ggaacgaagg tttccctaat agtaatttgt          2928
Thr Lys Met gtgaaagttc tggtagtctg tcagttcgga gagttaagaa aaaaaaaaaa cccccccccc    2988
cccccccccc ccccctggg tacgatcctc tagagtcggg agatggggga ggctaactga     3048
aacacggaag gagacaatac cggaaggaac ccgcgctatg acggcaataa aaagacagaa    3108
taaaacgcac gggtgttggg tcgtttgttc ataaacgcgg ggttcggtcc cagggctggc    3168
actctgtcga taccccaccg agaccccatt ggaccaata cgcccgcgtt tcttcctttt     3228
ccccacccca accccaagt tcgggtgaag gcccagggct cgcagccaac gtcgggggcgg    3288 caagccctgc catagccacg ggcccgtgg gttaggacg gggtcccca tgggaatgg        3348 tttatggttc gtggggtta ttattttggg cgttgcgtgg ggtcaggtcc acgactggac     3408
tgagcagaca gacccatggt ttttggatgg cctgggcatg gaccgcatgt actgcgcgca    3468
cacgaacacc gggcgtctgt ggctgccaaa caccccgac cccaaaaaac caccgcgcgg     3528
atttctggcg ccgccggacg tcgacttaat taacaagctt ag                      3570
```

<210> SEQ ID NO 2
<211> LENGTH: 564
<212> TYPE: PRT
<213> ORGANISM: Newcastle disease virus
<220> FEATURE:
<221> NAME/KEY: misc_feature
<222> LOCATION: (54)
<223> OTHER INFORMATION: Xaa = any amino acid

```
<400> SEQUENCE: 2

Met Asp Arg Ser Arg Leu Ala Pro Ser Arg Cys Arg Met Gly Ser Arg
 1               5                  10                  15

Pro Ser Thr Lys Asn Pro Ala Pro Met Met Leu Thr Ile Arg Val Ala
             20                  25                  30

Leu Val Leu Ser Cys Ile Cys Pro Ala Asn Ser Ile Asp Gly Arg Pro
         35                  40                  45

Leu Ala Ala Ala Gly Xaa Trp Leu Gln Glu Thr Lys Gln Ser Thr Tyr
     50                  55                  60

Thr Pro His Pro Arg Gln Val Asn His Ile Lys Leu Leu Pro Asn Leu
 65                  70                  75                  80

Pro Lys Asp Lys Glu Ala Cys Ala Lys Ala Pro Leu Asp Ala Tyr Asn
                 85                  90                  95

Arg Thr Leu Thr Thr Leu Leu Thr Pro Leu Gly Asp Ser Ile Arg Arg
            100                 105                 110

Ile Gln Glu Ser Val Thr Thr Ser Gly Gly Arg Gln Gly Arg Leu
        115                 120                 125

Ile Gly Ala Ile Ile Gly Gly Val Ala Leu Gly Val Ala Thr Ala Ala
    130                 135                 140

Gln Ile Thr Ala Ala Ala Leu Ile Gln Ala Lys Gln Asn Ala Ala
145                 150                 155                 160

Asn Ile Leu Arg Leu Lys Glu Ser Ile Ala Ala Thr Asn Glu Ala Val
                165                 170                 175

His Glu Val Thr Asp Gly Leu Ser Gln Leu Ala Val Ala Val Gly Lys
            180                 185                 190

Met Gln Gln Phe Val Asn Asp Gln Phe Asn Lys Thr Ala Gln Glu Leu
        195                 200                 205

Asp Cys Ile Lys Ile Ala Gln Gln Val Gly Val Glu Leu Asn Leu Tyr
    210                 215                 220

Leu Thr Glu Ser Thr Thr Val Phe Gly Pro Gln Ile Thr Ser Pro Ala
225                 230                 235                 240

Leu Asn Lys Leu Thr Ile Gln Ala Leu Tyr Asn Leu Ala Gly Gly Asn
                245                 250                 255

Met Asp Tyr Leu Leu Thr Lys Leu Gly Ile Gly Asn Asn Gln Leu Ser
            260                 265                 270

Ser Leu Ile Gly Ser Gly Leu Ile Thr Gly Asn Pro Ile Leu Tyr Asp
        275                 280                 285

Ser Gln Thr Gln Leu Leu Gly Ile Gln Val Thr Leu Pro Ser Val Gly
    290                 295                 300

Asn Leu Asn Asn Met Arg Ala Thr Tyr Leu Glu Thr Leu Ser Val Ser
305                 310                 315                 320

Thr Thr Arg Gly Phe Ala Ser Ala Leu Val Pro Lys Val Val Thr Arg
                325                 330                 335

Val Gly Ser Val Ile Glu Glu Leu Asp Thr Ser Tyr Cys Ile Glu Thr
            340                 345                 350

Asp Leu Asp Leu Tyr Cys Thr Arg Ile Val Thr Phe Pro Met Ser Pro
        355                 360                 365

Gly Ile Tyr Ser Cys Leu Ser Gly Asn Thr Ser Ala Cys Met Tyr Ser
    370                 375                 380

Lys Thr Glu Gly Ala Leu Thr Thr Pro Tyr Met Thr Ile Lys Gly Ser
385                 390                 395                 400
```

-continued

```
Val Ile Ala Asn Cys Lys Met Thr Thr Cys Arg Cys Val Asn Pro Pro
                405                 410                 415

Gly Ile Ile Ser Gln Asn Tyr Gly Glu Ala Val Ser Leu Ile Asp Lys
            420                 425                 430

Gln Ser Cys Asn Val Leu Ser Leu Gly Gly Ile Thr Leu Arg Leu Ser
        435                 440                 445

Gly Glu Phe Asp Val Thr Tyr Gln Lys Asn Ile Ser Ile Gln Asp Ser
    450                 455                 460

Gln Val Ile Ile Thr Gly Asn Leu Asp Ile Ser Thr Glu Leu Gly Asn
465                 470                 475                 480

Val Asn Asn Ser Ile Ser Asn Ala Leu Asn Lys Leu Glu Glu Ser Asn
                485                 490                 495

Arg Lys Leu Asp Lys Val Asn Val Lys Leu Thr Ser Thr Ser Ala Leu
            500                 505                 510

Ile Thr Tyr Ile Val Leu Thr Ile Ile Ser Leu Val Phe Gly Ile Leu
        515                 520                 525

Ser Leu Ile Leu Ala Cys Tyr Leu Met Tyr Lys Gln Lys Ala Gln Gln
    530                 535                 540

Lys Thr Leu Leu Trp Leu Gly Asn Asn Thr Leu Asp Gln Met Arg Ala
545                 550                 555                 560

Thr Thr Lys Met

<210> SEQ ID NO 3
<211> LENGTH: 3605
<212> TYPE: DNA
<213> ORGANISM: Infectious Laryngotracheitis Virus
<220> FEATURE:
<221> NAME/KEY: CDS
<222> LOCATION: (585)..(1889)
<223> OTHER INFORMATION: ILTV glycoprotein D
<220> FEATURE:
<221> NAME/KEY: CDS
<222> LOCATION: (1997)..(3085)
<223> OTHER INFORMATION: ILTV glycoprotein I

<400> SEQUENCE: 3
ctaagcttgt taattaagtc gacggcagag tcgcagacgc ccctattgga cgtcaaaatt      60
gtagaggtga agttttcaaa cgatggcgaa gtaacggcga cttgcgtttc caccgtcaaa     120
tctccctata gggtagaaac taattggaaa gtagacctcg tagatgtaat ggatgaaatt     180
tctgggaaca gtcccgccgg ggtttttaac agtaatgaga aatggcagaa acagctgtac     240
tacagagtaa ccgatggaag aacatcggtc cagctaatgt gcctgtcgtg cacgagccat     300
tctccggaac cttactgtct tttcgacacg tctcttatag cgagggaaaa agatatcgcg     360
ccagagttat actttacctc tgatccgcaa acggcatact gcacaataac tctgccgtcc     420
ggcgttgttc cgagattcga atggagcctt aataatgttt cactgccgga atatttgacg     480
gccacgaccg ttgtttcgca taccgctggc caaagtacag tgtggaagag cagcgcgaga     540
gcaggcgagg cgtggatttc tggccgggga ggcaatatat acga atg cac cgt cct      596
                                                 Met His Arg Pro
                                                 1 cat ctc aga cgg cac tcg cgt tac tac gcg aaa gga gag gtg ctt aac      644
His Leu Arg Arg His Ser Arg Tyr Tyr Ala Lys Gly Glu Val Leu Asn
  5                  10                  15                  20 aaa cac atg gat tgc ggt gga aaa cgg tgc tgc tca ggc gca gct gta      692
Lys His Met Asp Cys Gly Gly Lys Arg Cys Cys Ser Gly Ala Ala Val
                 25                  30                  35 ttc act ctt ttc tgg act tgt gtc agg att atg cgg gag cat atc tgc      740
```

|  |  |
|---|---|
| Phe Thr Leu Phe Trp Thr Cys Val Arg Ile Met Arg Glu His Ile Cys<br>           40                   45                50 |  |
| ttt gta cgc aac gct atg gac cgc cat tta ttt ttg agg aat gct ttt<br>Phe Val Arg Asn Ala Met Asp Arg His Leu Phe Leu Arg Asn Ala Phe<br>      55                    60                   65 | 788 |
| tgg act atc gta ctg ctt tct tcc ttc gct agc cag agc acc gcc gcc<br>Trp Thr Ile Val Leu Leu Ser Ser Phe Ala Ser Gln Ser Thr Ala Ala<br>    70                    75                 80 | 836 |
| gtc acg tac gac tac att tta ggc cgt cgc gcg ctc gac gcg cta acc<br>Val Thr Tyr Asp Tyr Ile Leu Gly Arg Arg Ala Leu Asp Ala Leu Thr<br> 85                   90                95               100 | 884 |
| ata ccg gcg gtt ggc ccg tat aac aga tac ctc act agg gta tca aga<br>Ile Pro Ala Val Gly Pro Tyr Asn Arg Tyr Leu Thr Arg Val Ser Arg<br>                  105               110              115 | 932 |
| ggc tgc gac gtt gtc gag ctc aac ccg att tct aac gtg gac gac atg<br>Gly Cys Asp Val Val Glu Leu Asn Pro Ile Ser Asn Val Asp Asp Met<br>             120                  125               130 | 980 |
| ata tcg gcg gcc aaa gaa aaa gag aag ggg ggc cct ttc gag gcc tcc<br>Ile Ser Ala Ala Lys Glu Lys Glu Lys Gly Gly Pro Phe Glu Ala Ser<br>          135                140               145 | 1028 |
| gtc gtc tgg ttc tac gtg att aag ggc gac gac ggc gag gac aag tac<br>Val Val Trp Phe Tyr Val Ile Lys Gly Asp Asp Gly Glu Asp Lys Tyr<br>     150                 155                160 | 1076 |
| tgt cca atc tat aga aaa gag tac agg gaa tgt ggc gac gta caa ctg<br>Cys Pro Ile Tyr Arg Lys Glu Tyr Arg Glu Cys Gly Asp Val Gln Leu<br>165               170                175             180 | 1124 |
| cta tct gaa tgc gcc gtt caa tct gca cag atg tgg gca gtg gac tat<br>Leu Ser Glu Cys Ala Val Gln Ser Ala Gln Met Trp Ala Val Asp Tyr<br>             185                  190               195 | 1172 |
| gtt cct agc acc ctt gta tcg cga aat ggc gcg gga ctg act ata ttc<br>Val Pro Ser Thr Leu Val Ser Arg Asn Gly Ala Gly Leu Thr Ile Phe<br>                  200               205              210 | 1220 |
| tcc ccc act gct gcg ctc tct ggc caa tac ttg ctg acc ctg aaa atc<br>Ser Pro Thr Ala Ala Leu Ser Gly Gln Tyr Leu Leu Thr Leu Lys Ile<br>     215                 220               225 | 1268 |
| ggg aga ttt gcg caa aca gct ctc gta act cta gaa gtt aac gat cgc<br>Gly Arg Phe Ala Gln Thr Ala Leu Val Thr Leu Glu Val Asn Asp Arg<br>230                   235               240 | 1316 |
| tgt tta aag atc ggg tcg cag ctt aac ttt tta ccg tcg aaa tgc tgg<br>Cys Leu Lys Ile Gly Ser Gln Leu Asn Phe Leu Pro Ser Lys Cys Trp<br>245               250                255             260 | 1364 |
| aca aca gaa cag tat cag act gga ttt caa ggc gaa cac ctt tat ccg<br>Thr Thr Glu Gln Tyr Gln Thr Gly Phe Gln Gly Glu His Leu Tyr Pro<br>             265                  270               275 | 1412 |
| atc gca gac acc aat aca cga cac gcg gac gac gta tat cgg gga tac<br>Ile Ala Asp Thr Asn Thr Arg His Ala Asp Asp Val Tyr Arg Gly Tyr<br>                  280               285              290 | 1460 |
| gaa gat att ctg cag cgc tgg aat aat ttg ctg agg aaa aag aat cct<br>Glu Asp Ile Leu Gln Arg Trp Asn Asn Leu Leu Arg Lys Lys Asn Pro<br>     295                 300               305 | 1508 |
| agc gcg cca gac cct cgt cca gat agc gtc ccg caa gaa att ccc gct<br>Ser Ala Pro Asp Pro Arg Pro Asp Ser Val Pro Gln Glu Ile Pro Ala<br>310               315                320 | 1556 |
| gta acc aag aaa gcg gaa ggg cgc acc ccg gac gca gaa agc agc gaa<br>Val Thr Lys Lys Ala Glu Gly Arg Thr Pro Asp Ala Glu Ser Ser Glu<br>325               330                335             340 | 1604 |
| aag aag gcc cct cca gaa gac tcg gag gac gac atg cag gca gag gct<br>Lys Lys Ala Pro Pro Glu Asp Ser Glu Asp Asp Met Gln Ala Glu Ala<br>             345                  350               355 | 1652 |

-continued

```
tct gga gaa aat cct gcc gcc ctc ccc gaa gac gac gaa gtc ccc gag    1700
Ser Gly Glu Asn Pro Ala Ala Leu Pro Glu Asp Asp Glu Val Pro Glu
        360                 365                 370 gac acc gag cac gat gat cca aac tcg gat cct gac tat tac aat gac    1748
Asp Thr Glu His Asp Asp Pro Asn Ser Asp Pro Asp Tyr Tyr Asn Asp
        375                 380                 385 atg ccc gcc gtg atc ccg gtg gag gag act act aaa agt tct aat gcc    1796
Met Pro Ala Val Ile Pro Val Glu Glu Thr Thr Lys Ser Ser Asn Ala
    390                 395                 400 gtc tcc atg ccc ata ttc gcg gcg ttc gta gcc tgc gcg gtc gcg ctc    1844
Val Ser Met Pro Ile Phe Ala Ala Phe Val Ala Cys Ala Val Ala Leu
405                 410                 415                 420 gtg ggg cta ctg gtt tgg agc atc gta aaa tgc gcg cgt agc taa        1889
Val Gly Leu Leu Val Trp Ser Ile Val Lys Cys Ala Arg Ser
                425                 430 tcgagcctag aataggtggt ttcttcctac atgccacgcc tcacgctcat aatataaatc  1949
acatggaata gcataccaat gcctattcat tgggacgttc gaaaagc atg gca tcg    2005
                                                    Met Ala Ser
                                                        435 cta ctt gga act ctg gct ctc ctt gcc gcg acg ctc gca ccc ttc ggc    2053
Leu Leu Gly Thr Leu Ala Leu Leu Ala Ala Thr Leu Ala Pro Phe Gly
        440                 445                 450 gcg atg gga atc gtg atc act gga aat cac gtc tcc gcc agg att gac    2101
Ala Met Gly Ile Val Ile Thr Gly Asn His Val Ser Ala Arg Ile Asp
455                 460                 465 gac gat cac atc gtg atc gtc gcg cct cgc ccc gaa gct aca att caa    2149
Asp Asp His Ile Val Ile Val Ala Pro Arg Pro Glu Ala Thr Ile Gln
470                 475                 480                 485 ctg cag cta ttt ttc atg cct ggc cag aga ccc cac aaa ccc tac tca    2197
Leu Gln Leu Phe Phe Met Pro Gly Gln Arg Pro His Lys Pro Tyr Ser
            490                 495                 500 gga acc gtc cgc gtc gcg ttt cgg tct gat ata aca aac cag tgc tac    2245
Gly Thr Val Arg Val Ala Phe Arg Ser Asp Ile Thr Asn Gln Cys Tyr
            505                 510                 515 cag gaa ctt agc gag gag cgc ttt gaa aat tgc act cat cga tcg tct    2293
Gln Glu Leu Ser Glu Glu Arg Phe Glu Asn Cys Thr His Arg Ser Ser
        520                 525                 530 tct gtt ttt gtc ggc tgt aaa gtg acc gag tac acg ttc tcc gcc tcg    2341
Ser Val Phe Val Gly Cys Lys Val Thr Glu Tyr Thr Phe Ser Ala Ser
535                 540                 545 aac aga cta acc gga cct cca cac ccg ttt aag ctc act ata cga aat    2389
Asn Arg Leu Thr Gly Pro Pro His Pro Phe Lys Leu Thr Ile Arg Asn
550                 555                 560                 565 cct cgt ccg aac gac agc ggg atg ttc tac gta att gtt cgg cta gac    2437
Pro Arg Pro Asn Asp Ser Gly Met Phe Tyr Val Ile Val Arg Leu Asp
                570                 575                 580 gac acc aaa gaa ccc att gac gtc ttc gcg atc caa cta tcg gtg tat    2485
Asp Thr Lys Glu Pro Ile Asp Val Phe Ala Ile Gln Leu Ser Val Tyr
        585                 590                 595 caa ttc gcg aac acc gcc gcg act cgc gga ctc tat tcc aag gct tcg    2533
Gln Phe Ala Asn Thr Ala Ala Thr Arg Gly Leu Tyr Ser Lys Ala Ser
            600                 605                 610 tgt cgc acc ttc gga tta cct acc gtc caa ctt gag gcc tat ctc agg    2581
Cys Arg Thr Phe Gly Leu Pro Thr Val Gln Leu Glu Ala Tyr Leu Arg
615                 620                 625 acc gag gaa agt tgg cgc aac tgg caa gcg tac gtt gcc acg gag gcc    2629
Thr Glu Glu Ser Trp Arg Asn Trp Gln Ala Tyr Val Ala Thr Glu Ala
630                 635                 640                 645 acg acg acc agc gcc gag gcg aca acc ccg acg ccc gtc act gca acc    2677
```

-continued

```
Thr Thr Thr Ser Ala Glu Ala Thr Thr Pro Thr Pro Val Thr Ala Thr
                650                 655                 660 agc gcc tcc gaa ctt gaa gcg gaa cac ttt acc ttt ccc tgg cta gaa     2725
Ser Ala Ser Glu Leu Glu Ala Glu His Phe Thr Phe Pro Trp Leu Glu
            665                 670                 675 aat ggc gtg gat cat tac gaa ccg aca ccc gca aac gaa aat tca aac     2773
Asn Gly Val Asp His Tyr Glu Pro Thr Pro Ala Asn Glu Asn Ser Asn
        680                 685                 690 gtt act gtc cgt ctc ggg aca atg agc cct acg cta att ggg gta acc     2821
Val Thr Val Arg Leu Gly Thr Met Ser Pro Thr Leu Ile Gly Val Thr
    695                 700                 705 gtg gct gcc gtc gtg agc gca acg atc ggc ctc gtc att gta att tcc     2869
Val Ala Ala Val Val Ser Ala Thr Ile Gly Leu Val Ile Val Ile Ser
710                 715                 720                 725 atc gtc acc aga aac atg tgc acc ccg cac cga aaa tta gac acg gtc     2917
Ile Val Thr Arg Asn Met Cys Thr Pro His Arg Lys Leu Asp Thr Val
                730                 735                 740 tcg caa gac gac gaa gaa cgt tcc caa act aga agg gaa tcg cga aaa     2965
Ser Gln Asp Asp Glu Glu Arg Ser Gln Thr Arg Arg Glu Ser Arg Lys
            745                 750                 755 ttt gga ccc atg gtt gcg tgc gaa ata aac aag ggg gct gac cag gat     3013
Phe Gly Pro Met Val Ala Cys Glu Ile Asn Lys Gly Ala Asp Gln Asp
        760                 765                 770 agt gaa ctt gtg gaa ctg gtt gcg att gtt aac ccg tct gcg cta agc     3061
Ser Glu Leu Val Glu Leu Val Ala Ile Val Asn Pro Ser Ala Leu Ser
    775                 780                 785 tcg ccc gac tca ata aaa atg tga ttaagtctga atgtggctct ccaatcattt    3115
Ser Pro Asp Ser Ile Lys Met
790                 795 cgattctcta atctcccaat cctctcaaaa ggggcagtat cggacacgga ctgggagggg   3175
cgtacacgat agttatatgg tacagcagag gcctctgaac acttaggagg agaattcagc   3235
cggggagagc ccctgttgag taggcttggg agcatattgc aggatgaaca tgttagtgat   3295
agttctcgcc tcttgtcttg cgcgcctaac ttttgcgacg cgacacgtcc tctttttgga   3355
aggcactcag gctgtcctcg gggaagatga tcccagaaac gttccggaag ggactgtaat   3415
caaatggaca aaagtcctgc ggaacgcgtg caagatgaag gcggccgatg tctgctcttc   3475
gcctaactat tgctttcatg atttaattta cgacggagga aagaaagact gcccgcccgc   3535
gggacccctg tctgcaaacc tggtaatttt actaaagcgc ggcgaaagct tcccgggtta   3595
attaacgtac                                                          3605

<210> SEQ ID NO 4
<211> LENGTH: 434
<212> TYPE: PRT
<213> ORGANISM: Infectious Laryngotracheitis Virus

<400> SEQUENCE: 4

Met His Arg Pro His Leu Arg Arg His Ser Arg Tyr Tyr Ala Lys Gly
  1               5                  10                  15

Glu Val Leu Asn Lys His Met Asp Cys Gly Gly Lys Arg Cys Cys Ser
             20                  25                  30

Gly Ala Ala Val Phe Thr Leu Phe Trp Thr Cys Val Arg Ile Met Arg
         35                  40                  45

Glu His Ile Cys Phe Val Arg Asn Ala Met Asp Arg His Leu Phe Leu
     50                  55                  60

Arg Asn Ala Phe Trp Thr Ile Val Leu Leu Ser Ser Phe Ala Ser Gln
 65                  70                  75                  80
```

```
Ser Thr Ala Ala Val Thr Tyr Asp Tyr Ile Leu Gly Arg Arg Ala Leu
                85                  90                  95

Asp Ala Leu Thr Ile Pro Ala Val Gly Pro Tyr Asn Arg Tyr Leu Thr
            100                 105                 110

Arg Val Ser Arg Gly Cys Asp Val Val Glu Leu Asn Pro Ile Ser Asn
        115                 120                 125

Val Asp Asp Met Ile Ser Ala Ala Lys Glu Lys Glu Lys Gly Gly Pro
    130                 135                 140

Phe Glu Ala Ser Val Val Trp Phe Tyr Val Ile Lys Gly Asp Asp Gly
145                 150                 155                 160

Glu Asp Lys Tyr Cys Pro Ile Tyr Arg Lys Glu Tyr Arg Glu Cys Gly
                165                 170                 175

Asp Val Gln Leu Leu Ser Glu Cys Ala Val Gln Ser Ala Gln Met Trp
            180                 185                 190

Ala Val Asp Tyr Val Pro Ser Thr Leu Val Ser Arg Asn Gly Ala Gly
        195                 200                 205

Leu Thr Ile Phe Ser Pro Thr Ala Ala Leu Ser Gly Gln Tyr Leu Leu
    210                 215                 220

Thr Leu Lys Ile Gly Arg Phe Ala Gln Thr Ala Leu Val Thr Leu Glu
225                 230                 235                 240

Val Asn Asp Arg Cys Leu Lys Ile Gly Ser Gln Leu Asn Phe Leu Pro
                245                 250                 255

Ser Lys Cys Trp Thr Thr Glu Gln Tyr Gln Thr Gly Phe Gln Gly Glu
            260                 265                 270

His Leu Tyr Pro Ile Ala Asp Thr Asn Thr Arg His Ala Asp Asp Val
        275                 280                 285

Tyr Arg Gly Tyr Glu Asp Ile Leu Gln Arg Trp Asn Asn Leu Leu Arg
    290                 295                 300

Lys Lys Asn Pro Ser Ala Pro Asp Pro Arg Pro Asp Ser Val Pro Gln
305                 310                 315                 320

Glu Ile Pro Ala Val Thr Lys Lys Ala Glu Gly Arg Thr Pro Asp Ala
                325                 330                 335

Glu Ser Ser Glu Lys Lys Ala Pro Pro Glu Asp Ser Glu Asp Asp Met
            340                 345                 350

Gln Ala Glu Ala Ser Gly Glu Asn Pro Ala Ala Leu Pro Glu Asp Asp
        355                 360                 365

Glu Val Pro Glu Asp Thr Glu His Asp Pro Asn Ser Asp Pro Asp
    370                 375                 380

Tyr Tyr Asn Asp Met Pro Ala Val Ile Pro Val Glu Glu Thr Thr Lys
385                 390                 395                 400

Ser Ser Asn Ala Val Ser Met Pro Ile Phe Ala Ala Phe Val Ala Cys
                405                 410                 415

Ala Val Ala Leu Val Gly Leu Leu Val Trp Ser Ile Val Lys Cys Ala
            420                 425                 430

Arg Ser
```

<210> SEQ ID NO 5
<211> LENGTH: 362
<212> TYPE: PRT
<213> ORGANISM: Infectious Laryngotracheitis Virus

<400> SEQUENCE: 5

```
Met Ala Ser Leu Leu Gly Thr Leu Ala Leu Ala Ala Thr Leu Ala
 1               5                  10                  15
```

-continued

```
Pro Phe Gly Ala Met Gly Ile Val Ile Thr Gly Asn His Val Ser Ala
                20                  25                  30
Arg Ile Asp Asp Asp His Ile Val Ile Val Ala Pro Arg Pro Glu Ala
            35                  40                  45
Thr Ile Gln Leu Gln Leu Phe Phe Met Pro Gly Gln Arg Pro His Lys
        50                  55                  60
Pro Tyr Ser Gly Thr Val Arg Val Ala Phe Arg Ser Asp Ile Thr Asn
 65                  70                  75                  80
Gln Cys Tyr Gln Glu Leu Ser Glu Glu Arg Phe Glu Asn Cys Thr His
                85                  90                  95
Arg Ser Ser Val Phe Val Gly Cys Lys Val Thr Glu Tyr Thr Phe
            100                 105                 110
Ser Ala Ser Asn Arg Leu Thr Gly Pro Pro His Pro Phe Lys Leu Thr
            115                 120                 125
Ile Arg Asn Pro Arg Pro Asn Asp Ser Gly Met Phe Tyr Val Ile Val
        130                 135                 140
Arg Leu Asp Asp Thr Lys Glu Pro Ile Asp Val Phe Ala Ile Gln Leu
145                 150                 155                 160
Ser Val Tyr Gln Phe Ala Asn Thr Ala Ala Thr Arg Gly Leu Tyr Ser
                165                 170                 175
Lys Ala Ser Cys Arg Thr Phe Gly Leu Pro Thr Val Gln Leu Glu Ala
            180                 185                 190
Tyr Leu Arg Thr Glu Glu Ser Trp Arg Asn Trp Gln Ala Tyr Val Ala
        195                 200                 205
Thr Glu Ala Thr Thr Thr Ser Ala Glu Ala Thr Thr Pro Thr Pro Val
210                 215                 220
Thr Ala Thr Ser Ala Ser Glu Leu Glu Ala Glu His Phe Thr Phe Pro
225                 230                 235                 240
Trp Leu Glu Asn Gly Val Asp His Tyr Glu Pro Thr Pro Ala Asn Glu
                245                 250                 255
Asn Ser Asn Val Thr Val Arg Leu Gly Thr Met Ser Pro Thr Leu Ile
            260                 265                 270
Gly Val Thr Val Ala Ala Val Val Ser Ala Thr Ile Gly Leu Val Ile
        275                 280                 285
Val Ile Ser Ile Val Thr Arg Asn Met Cys Thr Pro His Arg Lys Leu
        290                 295                 300
Asp Thr Val Ser Gln Asp Glu Glu Arg Ser Gln Thr Arg Arg Glu
305                 310                 315                 320
Ser Arg Lys Phe Gly Pro Met Val Ala Cys Glu Ile Asn Lys Gly Ala
                325                 330                 335
Asp Gln Asp Ser Glu Leu Val Glu Leu Val Ala Ile Val Asn Pro Ser
            340                 345                 350
Ala Leu Ser Ser Pro Asp Ser Ile Lys Met
            355                 360
```

RECOMBINANT AVIAN HERPESVIRUS USEFUL IN VACCINE PRODUCTION

CROSS-REFERENCE TO RELATED APPLICATIONS

This application is a continuation of U.S. Ser. No. 09/881,457, filed Jun. 14, 2001 now U.S. Pat. No. 6,913,751, and claims priority under 35 U.S.C. § 120, the contents of which are hereby incorporated by reference in their entireties.

FIELD OF THE INVENTION

The present invention relates to recombinant herpesviruses and, more particularly to a novel avian herpesvirus (NAHV) suitable for use as a viral vector for vaccination of birds against disease.

BACKGROUND OF THE INVENTION

The ability to isolate DNA and clone such isolated DNA into bacterial plasmids has greatly expanded the approaches available to make viral vaccines. The methods used to make the present invention involve modifying cloned DNA sequences from various viral pathogens of animals, by insertions, deletions, single or multiple base changes, and subsequent insertions of these modified sequences into the genome of the virus. One utility of the addition of a foreign sequence is achieved when the foreign sequence encodes a foreign protein that is expressed during viral infection of the animal. The resulting live virus may then be used in a vaccine to elicit an immune response in a host animal and provide protection to the animal against disease. A virus with these characteristics is referred to as a viral vector, because it becomes a living vector that will carry and express the foreign protein in the host animal. In effect it becomes an elaborate delivery system for the foreign protein(s).

The application of recombinant DNA techniques to animal viruses in general has a recent history. The first viruses to be engineered have been those with the smallest genomes. For example, in the case of the papovaviruses, because these viruses are so small and cannot accommodate much extra DNA, their use in genetic engineering has been as defective replicons. Thus, foreign DNA sequence expression from these viruses requires a wild-type helper virus and is limited to cell culture systems. On the other hand, for adenoviruses, there is a small amount of nonessential DNA that can be replaced by foreign sequences limiting its utility as a vector.

Another group of viruses that have been engineered are the poxviruses. One member of this group, vaccinia, has been the subject of much research on foreign gene expression. Poxviruses are large DNA-containing viruses that replicate in the cytoplasm of the infected cell. They have a structure that is unique in that they do not contain any capsid that is based upon icosahedral symmetry or helical symmetry. The poxviruses are most likely to have evolved from bacterial-like microorganisms through the loss of function and degeneration. In part due to this uniqueness, the advances made in the genetic engineering of poxviruses cannot be directly extrapolated to other viral systems, including the avian herpesviruses. The utility of vaccinia as a vaccine vector is in question because of its close relationship to human smallpox and its known pathogenicity to humans. Thus, the use of host-specific avian herpesviruses is a preferred solution to vaccination of poultry. Viral vectoring techniques have been applied to the genomes of several avian herpesviruses (e.g. U.S. Pat. No. 6,121,043, U.S. Pat. No. 5,965,138, and WO06/736A2).

Marek's disease virus (MDV) is the causative agent of Marek's disease, which encompasses fowl paralysis, a common lymphoproliferative disease of chickens. MDV, a naturally occurring herpesvirus, infects bursa-derived and thymus-derived lymphocytes in chickens, and may subsequently induce a lymphoma of thymus-derived lymphocytes. MDV is a designation of a family of avian herpesviruses. For example, MDV (MDV1) is a virulent strain of herpesvirus in chickens, SB-1 (MDV2) is a naturally attenuated herpesvirus strain in chickens, and HVT (MDV3) is a nonpathogenic herpesvirus of turkey.

Since Marek's disease is contagious, the virus has become an important pathogen of chickens, particularly in an environment of large scale breeding such as in the poultry industry. The disease occurs most commonly in young chickens between 2 and 5 months of age. The prominent clinical signs are progressive paralysis of one or more of the extremities, incoordination due to paralysis of legs, drooping of the limb due to wing involvement, and a lowered head position due to involvement of the neck muscles. In acute cases, severe depression may result. In the case of highly oncogenic strains, there is characteristic bursal and thymic atrophy. In addition, there are lymphoid tumors affecting the gonads, lungs, liver, spleen, kidney and thymus (Mohanty and Dutta, *Veterinary Virology*, Lea and Febiger, pubs., Philadelphia, 1981).

Currently, Marek's disease is controlled by vaccination of embryos at 17-19 days of incubation, or one day old chicks. The principal vaccination method for MDV involves using naturally occurring strains of turkey herpesvirus (HVT) or conventionally attenuated Marek's disease virus (MDV). It would be advantageous to incorporate other antigens into this vaccination, but efforts to combine conventional vaccines have not proven satisfactory due to competition and immunosuppression between pathogens. The multivalent NAHV based vaccines engineered in this invention represent a novel way to simultaneously vaccinate against a number of different pathogens.

A foreign gene of interest targeted for insertion into the genome of NAHV may be obtained from any pathogenic organism of interest. Typically, the gene of interest will be derived from pathogens that in poultry cause diseases that have an economic impact on the poultry industry. The genes may be derived from organisms for which there are existing vaccines, and because of the novel advantages of the vectoring technology, the NAHV derived vaccines will be superior. In addition, the gene of interest may be derived from pathogens for which there is currently no vaccine but where there is a requirement for control of the disease. Typically, the gene of interest encodes immunogenic polypeptides of the pathogen, and may represent surface proteins, secreted proteins and structural proteins.

An avian pathogen that is a target for NAHV vectoring is infectious laryngotracheitis virus (ILTV). ILTV is a member of the herpesviridae family, and this pathogen causes an acute disease of chickens, which is characterized by respiratory depression, gasping, and expectoration of bloody exudate. Viral replication is limited to cells of the respiratory tract, where in the trachea the infection gives rise to tissue erosion and hemorrhage. In chickens, no drug has been effective in reducing the degree of lesion formation or in decreasing clinical signs. Vaccination of birds with various modified forms of the ILTV derived by cell passage and/or tedious regimes of administration have conferred acceptable protection in susceptible chickens. Because of the degree of attenuation of current ILT vaccines care must be taken to assure that the correct level of virus is maintained; enough to provide protection, but not enough to cause disease in the flock.

An additional target for the NAHV vectoring approach is Newcastle disease, an infectious, highly contagious and debilitating disease that is caused by the Newcastle disease virus (NDV). NDV is a single-stranded RNA virus of the paramyxovirus family. The various pathotypes of NDV (velogenic, mesogenic, lentogenic) differ with regard to the severity of the disease, the specificity and symptoms, but most types seem to infect the respiratory system and the nervous system. NDV primarily infects chickens, turkeys and other avian species. Historically vaccination has been used to prevent disease, but because of maternal antibody interferences, life-span of the bird and route of administration, the producer needs to adapt immunization protocols to fit specific needs.

SUMMARY OF THE INVENTION

The present invention is directed to a recombinant avian herpesvirus comprising a herpes virus of turkeys unique long and repeat viral genome region and a Marek's disease virus unique short viral genome region wherein at least one foreign DNA sequence is inserted within the US2 gene of the unique short region of the recombinant avian herpesvirus and wherein the foreign DNA sequence is capable of being expressed in a host cell. In a preferred embodiment, the foreign DNA sequence is selected from the group consisting of a Newcastle disease virus fusion gene, an infectious laryngotracheitis virus glycoprotein D gene, an infectious laryngotracheitis glycoprotein I gene, or combinations thereof.

In another embodiment, the present invention is directed to a vaccine against Marek's disease, Newcastle disease, and/or infectious laryngotracheitis. The vaccine comprises a recombinant avian herpesvirus comprising a herpes virus of turkeys unique long and repeat viral genome region and a Marek's disease virus unique short viral genome region wherein at least one foreign DNA sequence is inserted within the US2 gene of the unique short region of the recombinant avian herpesvirus and wherein the foreign DNA sequence is capable of being expressed in a host cell, and a suitable carrier. Preferably the foreign DNA sequence is selected from the group consisting of a Newcastle disease virus fusion gene, an infectious laryngotracheitis virus glycoprotein D gene, an infectious laryngotracheitis glycoprotein I gene, or combinations thereof.

The present invention is also directed to a method of immunizing an avian species against Marek's disease, Newcastle disease, and/or infectious laryngotracheitis by administering a vaccine of the present invention.

BRIEF DESCRIPTION OF FIGURES

FIG. 1 is a comparison of HVT, NAHV, and MDV BamHI endonuclease restriction enzyme maps. Restriction fragments are labeled alphabetically in decreasing order of size. The structure of each virus is indicated below the map. Repeats regions are shown as boxes (open=HVT derived, shaded=MDV derived) and the unique regions are shown as lines (single=HVT derived, double=MDV derived). TRL=terminal repeat long; IRL=internal repeat long; IRS=internal repeat short; TRS=terminal repeat short; UL=unique long region; US=unique short region FIG. 2 is a BamHI endonuclease restriction enzyme map of NAHV and the positions of subgenomic clones used in the NAHV construction. Restriction fragments are label alphabetically in decreasing order of size. In the NAHV genome, the fragment corresponding to HVT fragment B is denoted as fragment A' and the fragment corresponding to MDV fragment A is denoted as fragment B'.

DETAILED DESCRIPTION OF THE INVENTION

The present invention is directed to a recombinant novel avian herpesvirus virus (NAHV) optionally comprising a foreign DNA sequence inserted into a non-essential site in the NAHV genome. The foreign DNA sequence is capable of being expressed in a host cell infected with the recombinant NAHV and its expression is under the control of a promoter located upstream of the foreign DNA sequence. The foreign DNA sequence encodes a polypeptide, which is antigenic in an animal into which the recombinant NAHV is introduced. More particularly, the foreign DNA sequence is from Newcastle disease virus (NDV) or infectious laryngotracheitis virus (ILTV) and the non-essential site in the NAHV genome is the US2 gene.

We have created recombinant organisms consisting of the unique long (UL) and repeat regions of the herpesvirus of turkeys (HVT) and the unique short (US) region of Marek's disease virus (MDV). The genome structure of these recombinant organisms and their parental viruses are compared in FIG. 1. Since these organisms are distinctly different from both of their parent organisms, they represent a completely new type of organism, a novel avian herpesvirus (NAHV).

These NAHV provide for highly efficacious and safe vaccines that protect poultry from Marek's disease. They combine the strong protective response provided by antigens from their Marek's disease virus parent with the established safety of their herpesvirus of turkeys parent. The NAHV-based vaccines exhibit increased protection against very virulent strains of MDV relative to HVT-based vaccines. However the NAHV-based vaccines retain the same non-pathogenic non-oncogenic safety profile of HVT.

The NAHV may also be used to create multivalent vaccines against Marek's disease, infectious laryngotracheitis, infectious bursal disease, Newcastle disease, or other poultry diseases. Multivalent viral vaccine strains are created by genetically engineering the NAHV to express antigens from the appropriate disease-causing organism. Several examples of NAHV-based vaccines are described below (examples 1-3).

As defined herein "a non-essential site in the NAHV genome" means a region in the NAHV viral genome, which is not necessary for the viral infection or replication. A "viral genome" or "genomic DNA" means the entire DNA, which the naturally occurring herpesvirus contains. As defined herein, "foreign DNA sequence" or "gene" means any DNA or gene that is exogenous to the genomic DNA. An "open reading frame" is a segment of DNA, which contains codons that can be transcribed into RNA which can be translated into an amino acid sequence and which does not contain a termination codon.

An "immunological composition" of the invention, as used herein, refers to any composition that elicits an immune response in an animal. An immune response is the reaction of the body to foreign substances, without implying a physiologic or pathologic consequence of such a reaction, i.e., without necessarily conferring protective immunity on the animal. An immune response may include one or more of the following: (a) a cell mediated immune response, which involves the production of lymphocytes by the thymus (T cells) in response to exposure to the antigen; and/or (b) a humoral immune response, which involves production of plasma lymphocytes (B cells) in response to antigen exposure with subsequent antibody production. The term "vaccine", as used herein, broadly refers to any compositions that may be administered to an animal to protect the animal against an infectious disease.

The invention further provides a recombinant NAHV suitable for use as a vaccine against Marek's disease. One example of such a virus is designated NAHV 295-01. This virus is also known as S-HVY-165. The recombinant avian herpesvirus designated NAHV 295-01 is a superior virus vaccine strain against very virulent Marek's disease, in chickens and turkeys, providing the safety of avirulent HVT, with the improved antigenicity of added MDV genes. The NAHV 295-01 recombinant virus vaccine is a superior virus vaccine because a single virus vaccine strain will protect against very virulent MDV. Currently the industry relies on combinations of vaccine strains. Since the NAHV 295-01 virus vaccine strain is genetically defined, it provides superior safety compared to conventional vaccine strains that risk reversion to virulence.

The present invention also provides a recombinant NAHV suitable for use as a vaccine containing a foreign DNA sequence encoding an antigenic polypeptide from NDV. In such case, it is preferred that the antigenic polypeptide is NDV fusion (F) protein. One example of such a virus is designated NAHV/NDV 295-93. This virus is also known as S-HVY-177. The recombinant avian herpesvirus designated NAHV/NDV 295-93 is a multivalent virus vaccine strain against Newcastle disease and very virulent Marek's disease in chickens. It contains a foreign gene encoding the fusion protein of the Newcastle disease virus inserted into the MDV US2 gene of the NAHV.

This recombinant virus vaccine has multiple advantages over conventional vaccines. The NAHV/NDV 295-93 vaccine can be administered in ovo without the interference often seen when conventional MDV and NDV vaccines are used. Since the vaccine lacks any NDV virulence genes there is no possibility of reversion to virulence or vaccine induced Newcastle disease. Additionally, the cell-associated nature of the NAHV backbone provides protection from NDV maternal antibody interference. The NAHV/NDV 295-93 recombinant virus vaccine is a superior Marek's disease virus vaccine because a single virus vaccine strain will protect against very virulent MDV. Currently the industry relies on combinations of vaccine strains. Since the NAHV/NDV 295-93 virus vaccine strain is genetically defined, it provides superior safety compared to conventional Marek's vaccine strains that risk reversion to virulence.

The invention further provides recombinant NAHV containing foreign DNA sequence encodes the antigenic polypeptide from an ILTV and encodes ILTV glycoprotein I and/or ILTV glycoprotein D. One example of such a virus is designated NAHV/ILT 295-149. This virus is also known as S-HVY-176.

The recombinant avian herpesvirus designated NAHV/ILT 295-149 is a multivalent virus vaccine strain against infectious laryngotracheitis and very virulent Marek's disease in chickens. It contains two foreign genes encoding glycoprotein D and glycoprotein I of the infectious laryngotracheitis virus inserted into the MDV US2 gene of the NAHV. This recombinant virus vaccine has multiple advantages over conventional vaccines. The NAHV/ILT 295-149 vaccine can be administered in ovo providing increased efficiency. Since the vaccine lacks any ILTV virulence genes there is no possibility of reversion to virulence or vaccine induced laryngotracheitis. The NAHV/ILT 295-149 recombinant virus vaccine is a superior Marek's disease virus vaccine because a single virus vaccine strain will protect against very virulent MDV. Currently the industry relies on combinations of vaccine strains. Since the NAHV/ILT 295-149 virus vaccine strain is genetically defined, it provides superior safety compared to conventional Marek's vaccine strains that risk reversion to virulence.

The novel recombinant avian herpesviruses of the present invention may be used as vaccines or immunological compositions against avian diseases which comprise an effective immunizing amount of a recombinant NAHV of the present invention and a suitable carrier. This invention provides a vaccine useful for immunizing an avian species against Marek's disease, which comprises an effective immunizing amount of the recombinant NAHV, and a suitable carrier.

This invention provides a vaccine useful for immunizing an avian species against Newcastle disease, which comprises an effective immunizing amount of the recombinant NAHV, and a suitable carrier.

This invention provides a vaccine useful for immunizing an avian species against infectious laryngotracheitis, which comprises an effective immunizing amount of the recombinant NAHV, and a suitable carrier.

This invention provides a multivalent vaccine useful for immunizing an avian species against Marek's disease and Newcastle disease, which comprises an effective immunizing amount of the recombinant NAHV and a suitable carrier.

This invention provides a multivalent vaccine useful for immunizing an avian species against Marek's disease and infectious laryngotracheitis, which comprises an effective immunizing amount of the recombinant NAHV and a suitable carrier.

Vaccines of the invention may be combined with other vaccines for other diseases to produce multivalent vaccines. For example, the present invention includes, a multivalent vaccine useful for immunizing an avian species against Marek's disease, Newcastle disease and infectious laryngotracheitis, which comprises a mixture of a first recombinant NAHV, a second recombinant NAHV, and a suitable carrier. One example of such a mixture comprises a first recombinant avian herpesvirus designated NAHV/ILT 295-149, a second recombinant avian herpesvirus designated NAHV/NDV 295-93, and a suitable carrier.

This invention provides an immunological composition which comprises at least one recombinant NAHV and a suitable carrier that elicits an immune response in a host avian species. The immune response can be local or systemic. The immune response can be protective or not be protective.

This invention provide recombinant NAHV, which express foreign DNA, sequences and are useful as vaccines in avian species including but not limited to chickens, turkeys, and ducks. These vaccines may contain either inactivated or live recombinant virus. These vaccines may contain infected cells. The vaccines of the present invention are administered by any of the methods well known to those skilled in the art, for example, by intramuscular, subcutaneous, intraperitoneal, or intravenous injection. The vaccine can be administered in ovo. Additional methods for administration of the vaccine well known to those skilled in the art are, for example, intranasally, intraocularly or orally.

For purposes of this invention, the term an "effective immunizing amount" refers to the amount of a substance that is sufficient to produce or elicit an immune response. For the present invention, an "effective immunizing amount" of the recombinant NAHV within the range of $10^2$ to $10^9$ PFU/dose. In another embodiment the immunizing amount is $10^2$ to $10^9$ PFU/dose. In a preferred embodiment the immunizing amount is approximately 2000 PFU/dose.

This invention provides methods for vaccination of avian species against disease. The method comprises administering to the animal an effective immunizing dose of the vaccine of the present invention. This invention provides a method for vaccination of an avian species against Marek's disease. It provides a method for vaccination of an avian species Newcastle disease. The present invention provides a method for vaccination of an avian species against infectious laryngotracheitis.

This invention provides methods for the vaccination of an avian species against more than one disease. The diseases can be caused by more than one pathogen. A method is provided for the vaccination of an avian species against Marek's disease and Newcastle disease. The present invention provides a method for vaccination of an avian species against Marek's disease and infectious laryngotracheitis. It also provides a method for vaccination of an avian species against Marek's disease, Newcastle disease and infectious laryngotracheitis.

The term "carrier" refers to a diluent, adjuvant, excipient or vehicle with which a compound is administered. Suitable carriers for the recombinant virus are well known to those skilled in the art and include but are not limited to sterile water, aqueous saline solutions, aqueous dextrose or glycerol solutions, proteins, sugars, etc. One example of such a suitable carrier is a physiologically balanced culture medium containing one or more stabilizing agents such as dimethyl sulfoxide, hydrolyzed proteins, lactose, etc.

This invention is further illustrated in the Methods and Examples sections, which follow. These sections are set forth to aid in an understanding of the invention but is not intended to, and should not be construed to, limit in any way the invention as set forth in the claims which follow thereafter.

Methods

Methods for constructing, selecting and purifying recombinant novel avian herpesviruses are detailed below in the materials, methods and examples. The following serve to illustrate certain preferred embodiments and aspects of the present invention and are not to be construed as limiting the scope thereof.

Preparation of NAHV Vaccine and Viral Stocks

Novel avian herpesvirus stock samples were prepared by infecting tissue culture cells at a multiplicity of infection of approximately 0.01 PFU/cell in complete F10/199 medium. All incubations were carried out at 39° C. in a humidified incubator with 5% $CO_2$ in air. This medium is composed of a 1:1 mixture of Medium 199 and Nutrient Mixture F10 Ham, 2 mM glutamine, 100 units/ml penicillin, 100 units/ml streptomycin, 1×MEM non-essential amino acids (these components are obtained from BioWhittaker or an equivalent supplier) plus 1% fetal bovine serum. After cytopathic effect was complete, the medium and cells were harvested and the cells were pelleted at 3000 rpm for 5 minutes in a clinical centrifuge. Infected cells were resuspended in complete medium containing 20% fetal bovine serum, 7% dimethyl sulfoxide (DMSO) and stored frozen at −70° C. For long term storage and shipping virus stocks were stored under liquid nitrogen or in the vapor phase of liquid nitrogen.

Preparation of Poultry Herpesvirus DNA

For the preparation of HVT, MDV and NAHV genomic DNA from the cytoplasm of infected cells, primary chicken embryo fibroblasts were infected at a MOI sufficient to cause extensive cytopathic effect before the cells overgrew. All incubations were carried out at 39° C. in a humidified incubator with 5% $CO_2$ in air. Best DNA yields were obtained by harvesting monolayers maximally infected, but showing incomplete cell lysis (typically 5-7 days). Infected cells were harvested by scraping the cells into the medium using a cell scraper (Costar brand). The cell suspension was centrifuged at 3000 rpm for 10 minutes at 5° C. in a GS-3 rotor (Sorvall Instruments). The resultant pellet was resuspended in cold PBS (Dulbecco's Phosphate Buffered Saline, 10 ml/225 $cm^2$ flask) and subjected to another centrifugation for 10 minutes at 3000 rpm in the cold. After decanting the PBS, the cellular pellet was resuspended in 2 ml/flask of cold RSB buffer (10 mM Tris pH 7.5, 1 mM ethylene diamine tetraacetic acid, disodium salt (EDTA), and 1.5 mM $MgCl_2$). One hundred μl of 20% SDS (5 mM final) was added and mixed by rocking. The sample was poured into a 15 ml conical tube. Tewenty-four μl of Proteinase K was added and mixed by rocking, then incubated at 50° C. for ≧1 hr. After this period, an equal volume of water-saturated phenol was added to the sample and gently mixed by hand. The sample was spun in a clinical centrifuge for 5 minutes at 3000 rpm to separate the phases. The aqueous layer containing the DNA was transferred to a fresh 15 ml conical tube and the phenol extraction repeated a second time. The aqueous layer containing the DNA was then transferred to a 15 ml corex tube and precipitated by adding one-tenth volume of 3 M sodium acetate (NaAC) and 2.5 volumes of cold 100% ethanol (EtOH). The DNA was pelleted by centrifigation (Sorval, HB4 swinging bucket rotor, 10,000 rpm, 20-30 minutes, 4° C.). The DNA pellet was washed with 80% EtOH and centrifuged again for 10 minutes. The pellet was air dried and resuspended in 300 μl TE. All viral DNA was stored at approximately 4° C.

Molecular-Biological Techniques

Techniques for the manipulation of bacteria and DNA, including such procedures as digestion with restriction endonucleases, gel electrophoresis, extraction of DNA from gels, ligation, phosphorylation with kinase, treatment with phosphatase, growth of bacterial cultures, transformation of bacteria with DNA, and other molecular biological methods are described by Maniatis et al (*Molecular Cloning*, Cold Spring Harbor Laboratory, New York, 1982) and Sambrook et al (*Molecular Cloning A Laboratory Manual Second Edition*, Cold Spring Harbor Press, 1989). The polymerase chain reaction (PCR) was used to introduce restriction sites convenient for the manipulation of various DNAs. The procedures used are described by Innis et al (*PCR Protocols A Guide to Methods and Applications,* 84-91, Academic Press, Inc., San Diego, 1990). In general, amplified fragments were less than 500 base pairs in size and critical regions of amplified fragments were confirmed by DNA sequencing. Except as noted these techniques were used with minor variation.

DNA Sequencing

DNA sequencing was performed on the Applied Biosystems Automated Sequencer Model 373A (with XL upgrade) per instructions of the manufacturer. Subclones were made to facilitate sequencing. Internal primers were synthesized on an ABI 392 DNA synthesizer or obtained commercially (Genosys Biotechnologies, Inc., The Woodlands, Tex.). Larger DNA sequences were built utilizing consecutive overlapping primers. Assembly, manipulation and comparison of sequences were performed with DNASTAR programs.

Procedure for Cloning NAHV Subgenomic DNA Fragments

A library of subclones containing overlapping HVT subgenomic fragments was generated as follows. DNA was obtained from the FC-126 strain of HVT (American Type Culture Collection). It was sheared and then size selected on a glycerol gradient as described by van Zijl et al., (*Journal of Virology* 62, 2191-2195, 1988) with 40-50 kb fragments chosen as the insert population. The pooled fractions were diluted twofold with TE (10 mM Tris pH 7.5, 1 mM EDTA), one-tenth volume of 3M NaAc and 2.5 volumes of ethanol were added, and the DNA was precipitated at 30K rpm in a Beckman SW41 rotor for 1 hr. The sheared fragments were given blunt ends by initial treatment with T4 DNA polymerase, using low dNTP concentrations to promote 3' overhang removal, followed by treatment with Klenow polymerase to fill in recessed 3' ends. These insert fragments were then ligated to a pWE15 (Strategene) cosmid vector, which had been digested with BamHI, treated with calf intestinal phosphatase, and made blunt by treatment with Klenow polymerase. The ligated mixture was then packaged using Gigapack XL packaging extracts (Stratagene). Ligation and packaging was as recommended by the manufacturer.

Published restriction maps for the enzymes BamHI, HindIII, and XhoI permitted the use of subcloned fragments as specific probes to screen the cosmid library for subclones spanning the genome. Probes were generated from subcloned restriction fragments. The fragments were then labeled using a non-radioactive system (Genius, Boehringer Mannheim). Screening was facilitated by picking colonies into media, followed by growth overnight. Sets of five filters and a master plate were stamped from microtiter dish and again grown overnight. Glycerol was added to the wells to 15% and the plates were frozen at −20° C. to provide stock cultures of each colony. Filters were BioRad Colony Lift Membranes and were treated and hybridized per manufacturer's instructions, and washed in 0.1×SSC, 0.1% SDS, 65° C. Positive clones, which hybridized with the non-radioactive probe, were detected according to the Genius kit directions.

Colonies were selected for further analysis on the basis of their hybridization to two or more of the specific probes. These were then digested with BamHI, and compared to published maps of HVT (Buckmaster et al., *J. Gen. Virol.* 69:2033, 1988). The three cosmids (407-32.2C3, 407-32.1C1, and 407-32.5G6) were obtained in this manner. A detailed description of each clone is given below. It was found that chloramphenicol amplification (Maniatis et al., *Molecular Cloning*, Cold Spring Harbor Laboratory, New York, 1982) was necessary to achieve reasonable yields of DNA from these clones. In addition, one cosmid clone (407-32.5G6) was unstable and had to be grown from the original frozen stock in order to obtain satisfactory DNA preparations.

The pWE15 vector allows the inserts to be excised with NotI. However, four NotI sites are present in the HVT genome, so that inserts spanning these sites cannot be excised with NotI. Two of the NotI sites are present in the BamHI B fragment of HVT, this fragment was cloned directly in pSP64 (clone 172-07.BA2). The other two sites are present in the unique short region within the BamHI A fragment. This fragment was cloned directly in the pWE15 vector. The three sheared cosmids and the two BamHI fragments cover all but a small portion of the ends of the HVT genome. Because these regions are repeated in the internal portions of the genome, all of the genetic information is available.

Marek's Disease Virus (MDV), GA strain, was obtained from the USDA (Agricultural Research Service Regional Poultry Laboratory, East Lansing, Mich.). In order to clone the short region, a partial SmaI digest of the DNA was performed and run out on a 0.6% low melt agarose gel. DNA fragments running greater than 24 kb were chosen as the insert population and excised from the gel. The DNA contained within the gel slice was extracted by using warm phenol, centrifugation, and then the aqueous phase was precipitated with one-tenth volume of 3M NaAc, an equal volume of isopropanol and centrifugation at 30K rpm in a Beckman SW41 rotor for 15 minutes. The pelleted DNA was then rinsed with 80% EtOH, air dried and resuspended in $H_2O$. Since the SmaI enzyme leaves blunt ends on the isolated fragments, a blunt end pWE15 cosmid vector was prepared as above. The ligated mixture was then packaged using Gigapack Plus packaging extracts (Stratagene). Ligation and packaging was as recommended by the manufacturer. Colonies were selected for further analysis on the basis of their hybridization to a MDV gD specific probe, and comparison to the published restriction digestion maps.

Procedure for Generating Novel Avian Herpesvirus from Overlapping Subgenomic Fragments Overlapping subgenomic fragments were cotransfected into chicken embryo fibroblast (CEF) cells by calcium phosphate precipitation, resulting in the regeneration of the NAHV genome. The regeneration was mediated by homologous recombination across the overlapping regions of the fragments. First, cosmid and plasmid DNAs were linearized using an appropriate enzyme, and purified by phenol extraction and ethanol precipitation. Then, approximately one microgram of each linear fragment was combined in $H_2O$ (300 μl final volume) and 37 μl of a 2.5M $CaCl_2$ stock was added. Next, 340 μl of a 2× Hepes buffered saline solution (140 mM NaCl, 1.5 mM $Na_2HPO_4$, 50 mM HEPES (N-[2-hydroxyethyl]piperazine-N'-[2-ethanesulfonic acid]), pH 7.05) was added and gently mixed for one minute at room temperature, to allow a fine precipitate to form. The precipitated DNA was added to a subconfluent monolayer of secondary CEF cells, plate in a 6 cm dish and allowed to absorb to the cells for approximately three hours at 39° C. Media was removed and cells were exposed to a 15% (v/v) Glycerol/PBS solution for one minute. The glycerol solution was removed and the monolayer was washed 3 times with PBS. Monolayers were fed with maintenance media (F10/199, 1% fetal bovine serum (FBS), 2% glutamine, 1% non-essential amino acids (NEAA), 1% penicillin/streptomycin (P/S)), and incubated at 39° C. The next day media was replaced and incubation at 39° C. continued. Plaques were visible in three to four days. When cells became overcrowded, infected monolayers were passed up to a larger size dish to allow spread of the virus. For passage, media was aspirated, cells were rinsed twice with PBS, aspirated again, then 0.5 ml trypsin-EDTA was added and incubated for 1-3 minutes at room temperature. Cells were pipetted up and down and diluted to 5 ml with maintenance media. The mixture was transferred to a larger dish and incubated at 39° C. When approximately 70 to 80% cytopathic effect (CPE) was achieved the infected cells were harvested by trypsinizing the monolayer as described above, except the cells were resuspended in F10/M199 Complete Freezing media. Infected cells were placed on ice and DMSO was added to 7%. After 15 minutes on ice, the cells were frozen at −70° C.

Stocks were then plaque purified two times. For each purification, stocks were diluted 1:100,000 in maintenance media and plated on several 10 cm dishes of secondary CEFs. After allowing the infected cells to sit down overnight, the infecting media was removed and replaced with 10 ml of nutrient agarose (0.8% low melt agarose, Media 199, 1% FBS, 2% glutamine, 1% NEAA 1% P/S), melted and cooled to 42° C., then allowed to harden at room temperature. Plates were then incubated 5 days at 39° C., until plaques formed. Isolated plaques were then picked using a glass Pasteur pipette to make a plug in the agarose. The plug containing the plaque was transfered into 24-well dish of CEFs. The dish was incubated 3 days, then each well was passed to a 6-well dish, and then to a 6 cm dish in 3 more days. Cells were grown until a 50-75% cytopathic effect was seen, then harvested as above and frozen at −70° C. A second purification was the performed as described above to obtain the final stock.

Southern Blot Analysis of Novel Avian Herpesviruses

Total DNA was isolated from a virus stock as described above. One tenth of the resuspended DNA isolated from a flask, 30 µl, was digested in 60 µl volume. Digestions with appropriate restriction endonucleases were performed as directed by the manufacturer. Digested DNA was loaded into a single well on a 25 cm long 0.7% agarose gel, and run overnight at 45 volts. Gel buffer was 0.5×TBE (a 1:10 dilution of 5×TBE).

Southern blots were performed using Zetaprobe blotting membranes. The alkaline blotting technique for DNA capillary transfer was used exactly as described in the Zetaprobe instruction manual (Section 2.3). The standard hybridization protocol and subsequent washes are also described in the same manual (Section 4.1) except that the membranes are not dried after the final wash. The probe was labeled using the Genius™ non-radioactive DNA labeling and detection kit. Labeling was performed as described in the detection kit instruction manual under section I, "DNA labeling". One half of the labeled material was denatured by boiling, and added to the hybridization buffer. After the hybridization washes described above, the Zetaprobe filters were treated as described in section III, "Immunological Detection", of the Genius™ labeling kit protocol.

Black Plaque Assay for Foreign Gene Expression in Novel Avian Herpesvirus

To analyze expression of foreign antigens expressed by recombinant NAHV viruses, monolayers of CEF cells were infected with recombinant NAHV, overlaid with nutrient agarose media and incubated for 4-5 days at 39° C. Once plaques developed, the agarose overlay was removed from the dish, the monolayer rinsed 1× with PBS, fixed with 100% methanol for 10 minutes at room temperature and the cells air-dried. After re-hydrating the plate with PBS, the primary antibody was diluted to the appropriate dilution with Blotto (5% non-fat milk/50 mM Tris pH 7.5/154 mM NaCl) and incubated with the cell monolayer for 2 hours to overnight at room temperature. Unbound antibody was then removed from the cells by washing three times with PBS at room temperature. An alkaline phosphatase conjugated secondary antibody was diluted with Blotto and incubated with the cells for 2 hours at room temperature. Unbound secondary antibody was then removed by washing the cells three times with PBS at room temperature. Next, the monolayer was rinsed in color development buffer (100 mM Tris pH 9.5/1000 mM NaCl/50 mM $MgCl_2$), and then incubated 10 minutes to overnight at room temperature with freshly prepared substrate solution (0.3 mg/ml Nitro Blue tetrazolium+0.15 mg/ml 5-bromo-4-chloro-3-indolyl phosphatase in color development buffer.) Finally, the reaction was stopped by replacing the substrate solution with TE (10 mM Tris pH 7.5/1 mM EDTA). Plaques expressing the correct antigen stained a purplish-black color.

Newcastle Disease Virus (NDV) Fusion Gene cDNA Cloning cDNA cloning refers to the methods used to convert RNA molecules into DNA molecules. These methods are described in (U. Gubler and B. J Hoffman, Gene 25, 263-269, 1983). These methods may also be accomplished through the use of various commercially available cDNA cloning kits.

For cloning NDV mRNA, primary chicken embryo fibroblast (CEF) cells were infected at 5-10 plaque forming units per cell with the NDV B1 Hitchner strain (American Tissue Type Culture). When cytopathic effect was evident, but before total destruction, the medium was removed and the cells were lysed in 10 ml lysis buffer (4 M guanidine thiocyanate, 0.1% antifoam A, 25 mM sodium citrate pH 7.0, 0.5% N-lauroyl sarcosine, 0.1 M beta-metcaptoethanol). The cell lysate was poured into a sterilized Dounce homogenizer and homogenized on ice 8-10 times until the solution was homogenous. For RNA purification, 8 ml of cell lysate were gently layered over 3.5 ml of CsCl solution (5.7 M CsCl, 25 mM sodium citrate pH 7.0) in Beckman SW41 centrifuge tube. The samples were centrifuged for 18 hrs at 20° C. at 36000 rpm in a Beckman SW41 rotor. The tubes were put on ice and the supernatants from the tubes were carefully removed by aspiration to leave the RNA pellet undisturbed. The pellet was resuspended in 400 μl glass distilled water, and 2.6 ml of guanidine solution (7.5 M guanidine-HCL, 25 mM sodium citrate pH 7.0, 5 mM dithiothreitol) were added. The 0.37 volumes of 1 M acetic acid were added, followed by 0.75 volumes of cold ethanol and the sample was put at −20° C. for 18 hrs to precipitate RNA. The precipitate was collected by centrifugation in a Sorvall centrifuge for 10 min a 4° C. at 10000 rpm in an SS34 rotor. The pellet was dissolved in 1.0 ml distilled water, centrifuged at 13000 rpm, and the supernatant saved. RNA was re-extracted from the pellet 2 more times as above with 0.5 ml distilled water, and the supernatants were pooled. A 0.1 volume of 2 M potassium acetate solution was added to the sample followed by 2 volumes of cold ethanol and the sample was put at −20° C. for 18 hrs. The precipitated RNA was collected by centrifugation in the SS34 rotor at 4° C. for 10 min at 10000 rpm. The pellet was dissolved in 1 ml distilled water and the concentration taken by absorption at A260/280. The RNA was stored at −70° C.

mRNA containing polyadenylate tails (poly-A) was selected using oligo-dT cellulose (Pharmacia #27 5543-0). Three mg of total RNA was boiled and chilled and applied to the 100 mg oligo-dT cellulose column in binding buffer (0.1 M Tris pH 7.5, 0.5 M LiCl, 5 mM EDTA pH 8.0, 0.1% lithium dodecyl sulfate). The retained poly-A RNA was eluted from the column with elution buffer (5 mM Tris pH 7.5, 1 mM EDTA pH 8.0, 0.1% sodium dodecyl sulfate). This mRNA was reapplied to an oligo-dT column in binding buffer and eluted again in elution buffer. The sample was precipitated with 200 mM sodium acetate and 2 volumes cold ethanol at −20° C. for 18 hrs. The RNA was resuspended in 50 μl distilled water.

Ten µg poly-A RNA was denatured in 20 mM methyl mercury hydroxide for 6 min at 22° C. β-mercaptoethanol was added to 75 mM and the sample was incubated for 5 min at 22° C. The reaction mixture for first strand cDNA synthesis in 0.25 ml contained 1 µg oligo-dT primer (P-L Bio-chemicals) or 1 µg synthetic primer, 28 units placental ribonuclease inhibitor (Bethesda Research Labs #5518SA), 100 mM Tris pH 8.3, 140 mM KCl, 10 mM $MgCl_2$, 0.8 mM dATP, dCTP, dGTP, and dTTP (Pharmacia), 100 microcuries $^{32}$p-labeled dCTP (New England Nuclear #NEG-013H), and 180 units AMV reverse transcriptase (Molecular Genetics Resources #MG 101). The reaction was incubated at 42° C. for 90 min, and then was terminated with 20 mM EDTA pH 8.0. The sample was extracted with an equal volume of phenol/chloroform (1:1) and precipitated with 2 M ammonium acetate and 2 volumes of cold ethanol –20° C. for 3 hrs. After precipitation and centrifugation, the pellet was dissolved in 100 µl distilled water. The sample was loaded onto a 15 ml G-100 Sephadex column (Pharmacia) in buffer (100 mM Tris pH 7.5, 1 mM EDTA pH 8.0, 100 mM NaCl). The leading edge of the eluted DNA fractions was pooled, and DNA was concentrated by lyophilization until the volume was about 100 µl, then the DNA was precipitated with ammonium acetate plus ethanol as above.

The entire first strand sample was used for second strand reaction which followed the Gubler and Hoffman (1983) method except that 50 µg/ml dNTP's, 5.4 units DNA polymerase I (Boerhinger Mannheim #642-711), and 100 units/ml E. coli DNA ligase (New England Biolabs #205) in a total volume of 50 microliters were used. After second strand synthesis, the cDNA was phenol/chloroform extracted and precipitated. The DNA was resuspended in 110 µl distilled water, treated with 1 µg RNase A for 10 min at 22° C., and electrophoresed through a 1% agarose gel (Sigma Type II agarose) in 40 mM Tris-acetate pH 6.85. The gel was stained with ethidium bromide, and DNA in the expected size range was excised from the gel and electroeluted in 8 mM Tris-acetate pH 6.85. Electroeluted DNA was lyophilized to about 100 microliters, and precipitated with ammonium acetate and ethanol as above. The DNA was resuspended in 20 µl water.

Oligo-dC tails were added to the DNA to facilitate cloning. The reaction contained the DNA, 100 mM potassium cacodylate pH 7.2, 0.2 mM dithiothreitol, 2 mM $CaCl_2$, 80 µmoles dCTP, and 25 units terminal deoxynucleotidyl transferase (Molecular Genetic Resources #S1001) in 50 µl. After 30 min at 37° C., the reaction was terminated with 10 mM EDTA, and the sample was phenol/chloroform extracted and precipitated as above.

The dC-tailed DNA sample was annealed to 200 ng plasmid vector pBR322 that contained oligo-dG tails (Bethesda Research Labs #5355 SA/SB) in 200 µl of 0.01 M Tris pH 7.5, 0.1 M NaCl, 1 mM EDTA pH 8.0 at 65° C. for 2 min and then 57° C. for 2 hrs. Fresh competent E. coli DH-1 cells were prepared and transformed as described by Hanahan (*Molecular Biology* 166, 557-580, 1983) using half the annealed cDNA sample in twenty 200 µl aliquots of cells. Transformed cells were plated on L-broth agar plates plus 10 µg/ml tetracycline. Colonies were screened for the presence of inserts into the ampicillin gene using Ampscreen (Bethesda Research Labs #5537 UA), and the positive colonies were picked for analysis. Resulting positive clones were screened for homology to paramyxovirus fusion gene sequences. A clone containing the complete coding sequence of the NDV fusion gene was identified. The sequence of this clone is given in SEQ ID: 1.

Subgenomic Clone 407-32.2C3

Cosmid 407-32.2C3 contains an approximately 40,000 base pair region of genomic HVT DNA (from the left terminus to position 39,750 GenBank Accession No. AF291866, see FIG. 2). This region includes NAHV BamHI fragments F', L, P, N1, E, D, and 2,092 base pairs of fragment A'. Note: NAHV BamHI fragment A', is called fragment B in HVT. This cosmid may be constructed as described above in the Procedure for Cloning NAHV Subgenomic DNA Fragments. It was isolated from the sheared DNA library by screening with the probes P1 (HVT BamHI fragment F, position 116,948 to 125,961, Genbank Accession No. AF291866) and P2 (HVT BamHI fragment B, 37,663 to 63,593, Genbank Accession No. AF291866). A bacterial strain containing this cosmid has been deposited pursuant to the Budapest Treaty on the International Deposit of Microorganisms for the Purposes of Patent Procedure with the Patent Culture Depository of the American Type Culture Collection, 10801 University Boulevard, Manassas Va. 20010-2209 U.S.A. under ATCC Accession No. 75430.

Subgenomic Clone 172-07.BA2

Plasmid 172-07.BA2 contains a 25,947 base pair region of genomic HVT DNA. This plasmid was constructed using standard recombinant DNA techniques joining two restriction fragments from the following sources. The first fragment is a 2999 base pair BamHI to BamHI restriction fragment of pSP64 (Promega). The second fragment is the 25,947 base pair BamHI B fragment of HVT (position 37,663 to 63,593, GenBank Accession No. AF291866). Note: In the NAHV genome, this fragment is denoted as fragment A', due to size considerations.

Subgenomic Clone 407-32.5G6

Cosmid 407-32.5G6 contains a 39,404 base pair region of genomic HVT DNA (position 61,852 to 101,255, Genbank Accession No. AF291866). This region includes NAHV BamHI fragments H, C, Q, K1, M, K2, plus 1,742 base pairs of fragment A', and 3,880 base pairs of fragment J. Note: NAHV BamHI fragment A', is called fragment B in HVT. This cosmid was constructed as described above in the Procedure for Cloning NAHV Subgenomic DNA Fragments. It was isolated from the sheared DNA library by screening with the probes P2 (HVT BamHI fragment B, 37,663 to 63,593, Genbank Accession No. AF291866) and P3 (HVT BamHI fragment J, position 97,376 to 102,720, Genbank Accession No. AF291866). A bacterial strain containing this cosmid has been deposited on Mar. 3, 1993 pursuant to the Budapest Treaty on the International Deposit of Microorganisms for the Purposes of Patent Procedure with the Patent Culture Depository of the American Type Culture Collection, 10801 University Boulevard, Manassas Va. 20010-2209 U.S.A. under ATCC Accession No. 75427.

Subgenomic Clone 407-32.1C1

Cosmid 407-32.1C1 contains a 37,444 base pair region of genomic HVT DNA (position 96,095 to 133,538, GenBank Accession No. AF291866, see FIG. 2). This region includes NAHV BamHI fragments J., G, I, F, O, plus 1,281 base pairs of fragment K2, and 6,691 base pairs of fragment B'. Note: NAHV BamHI fragment B', is called fragment A in HVT. This cosmid was constructed as described above in the Procedure for Cloning NAHV Subgenomic DNA Fragments. It was isolated from the sheared DNA library by screening with the probes P1 (HVT BamHI fragment F, position 116,948 to 125,961, Genbank Accession No.

AF291866) and P4 (4169 base pair BglII to StuI subfragment (position 132,088 to 136,256, GenBank Accession No. AF291866) of HVT XhoI fragment #5 (position 128,950 to 136,510, GenBank Accession No. AF291866)). Note: an internal StuI site occurs within the 4169 base pair sub-fragment (position 134,083, GenBank Accession No. AF291866). However this site is methylated and does not cleave in plasmid DNA prepared from standard cloning strains of bacteria. A bacterial strain containing this cosmid has been deposited on Mar. 3, 1993 pursuant to the Budapest Treaty on the International Deposit of Microorganisms for the Purposes of Patent Procedure with the Patent Culture Depository of the American Type Culture Collection, 10801 Univesity Boulevard, Manassas Va., 20010-2209 U.S.A. under ATCC Accession No. 75428.

Subgenomic Clone 989-72.8#1

The cosmid 989-72-8#1 contains the NAHV short region cloned into the cosmid pWE15 (Stratagene). To create a short region cosmid for the NAHV, the US region of MDV was joined with the short repeat regions of HVT by PCR amplification and standard cloning techniques. In this engineered cosmid, the complete MDV US region was used, but the short repeat regions of HVT were shortened to remove the US8 (gE) sequence. This avoids the inclusion of sequence homologous to the US8 gene within the MDV US. Cosmid 989-72.8-1 contains the following DNAs: 9,193 bp of the short repeat region from HVT BamHI B (position 126,848 to 136,040; GenBank Accession No. AF291866), an 8 bp synthetic Pac-I linker, 11,156 bp from the MDV US (position 66 to 11,221, GenBank Accession L22174), an 8 bp synthetic Pac-I linker, and a second HVT short repeat (position 136,040 to 126,848, GenBank Accession No. AF291866), inverted relative to the other repeat. The pWE15 cosmid vector, used to clone these DNAs, was modified by replacing the 64 bp multiple cloning site (EcoRI to EcoRI), with a 68 bp synthetic linker (EcoRI, I-SceI, NotI, BamHI, NotI, I-SceI, and EcoRI), to allow excision of the insert with the I-SceI enzyme.

Foreign DNA sequences are added into the NAHV genome at a KpnI site with in the MDV US2 gene (position 4646, GenBank Accession L22174). The KpnI site interrupts this 270 amino acid coding region at approximately amino acid 85. Cloning the appropriate foreign DNA sequence into the NAHV short region cosmid, 989-72.8#1 at this KpnI site, creates Subgenomic clones used to introduce foreign genes.

Subgenomic Clone 1002-75.4

The cosmid 1002-75.4 contains a foreign gene encoding the fusion protein of the Newcastle disease virus inserted within the MDV US2 gene of the NAHV short region cosmid, 989-72.8#1. The NDV fusion gene (F) is under the control of the human cytomegalovirus immediate early (HCMV IE) promoter and utilizes the herpes simplex virus thymidine kinase (HSV tk) poly adenylation signal (pA). This cosmid was created using standard DNA cloning techniques. The sequence of the foreign DNA inserted into cosmid 989-72.8#1 is given in SEQ ID 1. This sequence was inserted such that the NDV F and MDV US2 genes are transcribed in the same direction. The source of each region of the insert is indicated in the following table.

TABLE 1

Source of foreign DNAs inserted into Subgenomic Clone 1002-75.4

| Region | Start[a] | End[b] | Source |
|---|---|---|---|
| 1 | 1 | 36 | Synthetic Linker |
| 2 | 37 | 1189 | HCMV genomic DNA (IE promoter cloned as described in U.S. Pat. No. 5,830,745 and sequenced as described above) |
| 3 | 1190 | 1200 | Synthetic linker |
| 4 | 1201 | 3004 | NDV cDNA (F gene cloned and sequenced as described above) |
| 5 | 3005 | 3025 | Synthetic linker |
| 6 | 3026 | 3548 | HSV genomic DNA (tk pA position 37,694 to 37,172 GenBank Accession No. D10879) |
| 7 | 3549 | 3570 | Synthetic linker |

[a]Starting position of the region in SEQ. ID NO: 1
[b]Ending position of the region in SEQ. ID NO: 1

Subgenomic Clone Vector 1012-89.2

The cosmid 1012-89.2 contains two foreign genes encoding the glycoprotein D and glycoprotein I of the infectious laryngotracheitis virus (ILTV) inserted in to the MDV US2 gene of the NAHV short region cosmid, 989-72.8#1. The ILTV genes are under the control of their endogenous promoters. This cosmid was created using standard DNA cloning techniques. The sequence of the foreign DNA inserted into cosmid 989-72.8#1 is given in SEQ ID 3. This sequence was inserted such that the ILTV gD gene and ILTV gI gene are transcribed in the opposite direction of the MDV US2 genes. The source of each region of the insert is indicated in the following table.

TABLE 2

Source of foreign DNAs inserted into Subgenomic Clone 1012-89.2

| Region | Start[a] | Stop[b] | Source |
|---|---|---|---|
| 1 | 1 | 18 | Synthetic Linker |
| 2 | 19 | 3581 | ILTV genomic DNA (gD and gI genes (position 10,532 to 14,094 Genbank Accession No. U28832) |
| 3 | 3582 | 3605 | Synthetic linker |

[a]Starting position of the region in SEQ. ID NO: 3
[b]Ending position of the region in SEQ. ID NO: 3

EXAMPLES

Example 1

The NAHV Designated NAHV 295-01 and the Marek's Disease Recombinant Vaccine (NAHV 295-01)

The NAHV 295-01 recombinant virus was generated according to the Procedure for Generating Novel Avian Herpesvirus from Overlapping Subgenomic Fragments. The following combination of subgenomic clones and enzymes were used: 989-72.8#1 with I-SceI, 407-32.2C3 with NotI, 172-07.BA2 with BamHI, 407-32.5G6 with NotI, and 407-32.1C1 with NotI. (The location of subgenomic clones on the resulting NAHV genome is indicated in FIG. 2.) The NAHV was shown to have the correct genomic structure using the Southern Blot Analysis of Novel Avian Herpesviruses. Stability of the NAHV 295-01 virus vaccine strain was demonstrated by serial passage 12 times in tissue culture followed by a second Southern blot analysis. This virus strain has been deposited on Jun. 13, 2001 pursuant to the Budapest Treaty on the International Deposit of Microorganisms for the Purposes of Patent Procedure with the Patent Culture Depository of the American Type Culture Collection, 10801 University Boulevard, Manassas Va. 20010-2209 U.S.A. under ATCC Accession No. PTA-3451.

The following studies were conducted to demonstrate the safety of the NAHV 295-01 vaccine, and its effectiveness in protecting against challenge with very virulent Marek's disease virus. In study 1,18-day-old specific pathogen free (SPF) embryos, or one-day-old chicks were vaccinated with the NAHV 295-01 vaccine. As controls, additional groups of one-day-old chicks were vaccinated with one of two USDA-licensed, conventional vaccines comprised of either HVT or MDV-1/Rispens. Five days post-hatch, vaccinated chicks, and non-vaccinated, control chicks were challenged with virulent MDV/RB 1B. Birds were then observed for clinical signs of disease for 7 weeks, then necropsied to examine for gross lesions. The results, in Table 3, show the NAHV 295-01 vaccine gave greater protection against very virulent Marek's disease challenge than either commercial vaccine.

TABLE 3

Efficacy of the NAHV 295-01 Recombinant Vaccine Against Virulent Marek's Disease Virus Challenge

| Group | Route | Dose[a] | Challenge[b] | Protection Ratio[c] | % Protected |
|---|---|---|---|---|---|
| Non-vac. | — | — | — | 25/25 | — |
| Non-vac. | — | — | RB1B | 1/30 | 3% |
| NAHV 295-01 | in ovo | 895 pfu | RB1B | 28/30 | 93% |
| NAHV 295-01 | SC | 940 pfu | RB1B | 29/30 | 97% |
| HVT | SC | As per label | RB1B | 18/30 | 60% |
| Rispens | SC | As per label | RB1B | 27/30 | 90% |

[a]in ovo dose: PFU/0.05 ml; SC dose: PFU/0.2 ml
[b]Challenge 5 days post-vaccination, intra-abdominal
[c]No. protected/Total on day 54

In the second study, 18-day-old embryos or one-day-old SPF chicks were vaccinated with ten times the maximum dose of the NAHV 295-01 vaccine. The chicks were observed for 120 days for clinical signs of Marek's disease, then necropsied and examined for Marek's lesions. As controls, a third group of birds remained un-vaccinated, and a fourth group of un-vaccinated birds was challenged on day 4 with virulent MDV/RB 1 B to demonstrate that the birds were susceptible to Marek's disease. The results, in Table 4, demonstrate the safety of the NAHV 295-01 vaccine given in ovo (18-day-old embryos) or at one day-of-age.

TABLE 4

Safety the NAHV 295-01 Recombinant Vaccine Following in ovo or Subcutaneous Injection with 10x Dose.

| Group | Route | Dose[a] | Challenge[b] | % MD[c] |
|---|---|---|---|---|
| Non-vac. | — | — | — | — |
| Non-vac. | — | — | RB1B | 100% |
| NAHV 295-01 | in ovo | 20,000 pfu | — | 0% |
| NAHV 295-01 | SC | 20,000 pfu | — | 0% |

[a]dose: PFU/0.05 ml (In ovo) or PFU/0.2 ml (SC).
[b]Challenge 5 days post-vaccination; intra-abdominal.
[c]Percentage MD positive/Total by day 120.

Example 2

The NAHV designated NAHV/NDV 295-93 and the Multivalent Marek's Disease/Newcastle Disease Recombinant Vaccine (NAHV/NDV 295-93)

The NAHV/NDV 295-93 recombinant virus was generated according to the Procedure for Generating Novel Avian Herpesvirus from Overlapping Subgenomic Fragments. The following combination of subgenomic clones and enzymes were used: 1002-75.4 with I-SceI, 407-32.2C3 with NotI, 172-07.BA2 with BamHI, 407-32.5G6 with NotI, and 407-32.1C1 with NotI. (The location of subgenomic clones on the resulting NAHV genome is indicated in FIG. 2.) The NAHV was shown to have the correct genomic structure using the Southern Blot Analysis of Novel Avian Herpesviruses. Stability of the NAHV/NDV 295-93 virus vaccine strain was demonstrated by serial passage 12 times in tissue culture followed by a second Southern blot analysis. This virus strain has been deposited on Jun. 13, 2001 pursuant to the Budapest Treaty on the International Deposit of Microorganisms for the Purposes of Patent Procedure with the Patent Culture Depository of the American Type Culture Collection, 10801 Univesity Boulevard, Manassas Va. 20010-2209 U.S.A. under ATCC Accession No. PTA-3453.

The Black Plaque Assay for Foreign Gene Expression in Novel Avian Herpesvirus was used to demonstrate expression of the NDV fusion gene. The assay used a monoclonal antibody directed to the NDV fusion gene (3-1 G5) diluted 1:100 as the primary antibody. A goat anti-mouse alkaline phosphatase conjugated antibody diluted 1:1000 was used as the secondary antibody. Purity of the virus was demonstrated by assay of serial passage 12 stocks, 97.6% (1029/1054) of the viral plaques were black plaque positive.

The following studies were conducted to demonstrate the effectiveness of the NAHV/NDV 295-93 vaccine, in protecting against challenge with either virulent Newcastle disease virus, or very virulent Marek's disease virus. In Study 1,18-day-old specific pathogen free (SPF) embryos, or one-day-old chicks were vaccinated with the NAHV/NDV 295-93 vaccine. As a control, a third group of one-day-old chicks remained un-vaccinated. Twenty-one days post-hatch, vaccinated chicks, and non-vaccinated, control chicks were challenged with virulent NDV/Texas GB strain. Birds were then observed for clinical signs of disease for fourteen days. The results, in Table 5, show the NAHV/NDV 295-93 vaccine gave better than 90% protection against virulent NDV.

TABLE 5

Efficacy of the NAHV/NDV 295-93 Recombinant Vaccine Against Virulent Newcastle Disease Virus Challenge

| Group | Route | Dose[a] | Challenge[b] | % Protected[c] |
|---|---|---|---|---|
| Non-vac. | — | — | — | — |
| Non-vac. | — | — | Texas GB | 0% |
| NAHV/NDV 295-93 | in ovo | 525 pfu | Texas GB | 90% |
| NAHV/NDV 295-93 | SC | 707 pfu | Texas GB | 97% |

[a]In ovo dose: PFU/0.05 ml; SC dose: PFU/0.2 ml.
[b]Challenge 21 days post-vaccination, intra-ocular.
[c]Percentage Protected/Total; 14 days post-challenge.

In study two, 18-day-old embryos, or one-day-old SPF chicks were vaccinated with the NAHV/NDV 295-93 vaccine. As controls, additional groups of one-day-old chicks were vaccinated with one of two USDA-licensed, conventional vaccines comprised of either HVT or MDV-1/Rispens. Five days post-hatch, vaccinated chicks, and non-vaccinated, control chicks were challenged with virulent MDV/RB1B. Birds were observed for clinical signs of disease for 7 weeks, then necropsied to examine for gross lesions. The results, in Table 6, show the NAHV/NDV 295-93 vaccine protected against very virulent Marek's disease challenge.

TABLE 6

Efficacy of the NAHV/NDV 295-93 Recombinant Vaccine Against Virulent Marek's Disease Virus Challenge

| Group | Route | Dose[a] | Challenge[b] | Protection Ratio[c] | % Protected |
|---|---|---|---|---|---|
| Non-vac. | — | — | — | 25/25 | — |
| Non-vac. | — | — | RB1B | 1/30 | 3% |
| NAHV/NDV 295-93 | in ovo | 675 pfu | RB1B | 28/30 | 93% |
| NAHV/NDV 295-93 | SC | 680 pfu | RB1B | 26/30 | 87% |
| HVT | SC | As per label | RB1B | 18/30 | 60% |
| Rispens | SC | As per label | RB1B | 27/30 | 90% |

[a]In ovo dose: PFU/0.05 ml; SC dose: PFU/0.2 ml.
[b]Challenge 5 days post-vaccination, intra-abdominal.
[c]No. protected/Total on day 54.

Example 3

The NAHV Designated NAHV/ILT 295-149 and the Multivalent Marek's Disease/Infectious Laryngotrachetitis Recombinant Vaccine (NAHV/ILT 295-149)

The NAHV/ILT 295-149 recombinant virus was generated according to the Procedure for Generating Novel Avian Herpesvirus from Overlapping Subgenomic Fragments. The following combination of subgenomic clones and enzymes were used: 1012-89.2 with I-SceI, 407-32.2C3 with NotI, 172-07.BA2 with BamHI, 407-32.5G6 with NotI, and 407-32.1C1 with NotI. (The location of subgenomic clones on the resulting NAHV genome is indicated in FIG. 2.) The NAHV was shown to have the correct genomic structure using the Southern Blot Analysis of Novel Avian Herpesviruses. Stability of the the NAHV/ILT 295-149 virus vaccine strain was demonstrated by serial passage 12 times in tissue culture followed by a second Southern blot analysis. This virus strain has been deposited on Jun. 13, 2001 pursuant to the Budapest Treaty on the International Deposit of Microorganisms for the Purposes of Patent Procedure with the Patent Culture Depository of the American Type Culture Collection, 10801 Univesity Boulevard, Manassas Va. 20010-2209 U.S.A. under ATCC Accession No. PTA-3452.

The Black Plaque Assay for Foreign Gene Expression in Novel Avian Herpesvirus was used to demonstrate expression of the ILT glycoproteins. The assay used a convalescent ILT chicken sera (SPAFAS, Inc.) diluted 1:100 as the primary antibody. A goat anti-chicken alkaline phosphatase conjugated antibody diluted 1:1000 was used as the secondary antibody. Purity of the virus was demonstrated by assay of serial passage 12 stocks. 99.4% (1043/1049) of the viral plaques were black plaque positive.

The following studies were conducted to demonstrate the effectiveness of the NAHV/ILT 295-149 vaccine, in protecting against challenge with either virulent infectious laryngotracheitis virus, or very virulent Marek's disease virus. In study 1, 18-day-old specific pathogen free (SPF) embryos, or one-day-old chicks were vaccinated with the NAHV/ILT 295-149 vaccine. As controls, additional groups of one-day-old chicks either remained un-vaccinated, or were vaccinated with a USDA-licensed, conventional vaccine comprised of attenuated, live ILTV (LT-Ivax). Twenty-five days post-hatch, vaccinated chicks, and non-vaccinated, control chicks were challenged with virulent ILT/USDA LT-96-3. Birds were observed for clinical signs of disease for ten days, and then necropsied to examine for gross lesions. The results, in Table 7, show the NAHV/ILT 295-149 vaccine gave better protection against virulent ILT than the commercial vaccine.

TABLE 7

Efficacy of the NAHV/ILT 295-149 Recombinant Vaccine Against Virulent Infectious Laryngotracheitis Virus Challenge

| Group | Route | Dose[a] | Challenge[b] | % Protected[c] |
|---|---|---|---|---|
| Non-vac. | — | — | — | — |
| Non-vac. | — | — | ILT(USDA) | 0% |
| NAHV/ILT 295-149 | in ovo | 750 pfu | ILT(USDA) | 100% |
| NAHV/ILT 295-149 | SC | 750 pfu | ILT(USDA) | 100% |
| LT-Ivax | Per label | Per label | ILT(USDA) | 60% |

[a]In ovo dose: PFU/0.05 ml; SC dose: PFU/0.2 ml.
[b]Challenge 25 days post-vaccination, intra-tracheal.
[c]Percentage Protected/Total; 10 days post-challenge In study two, 18-day-old embryos, or one-day-old SPF chicks were vaccinated with NAHV/ILT 295-149. As controls, additional groups of one-day-old chicks were vaccinated with a USDA-licensed, conventional vaccine comprised of MDV-1/Rispens, or left un-vaccinated. Five days post-hatch, vaccinated chicks, and non-vaccinated, control chicks were challenged with virulent MDV/RB1B. Birds were observed for clinical signs of disease for 7 weeks, then necropsied to examine for gross lesions. The results, in Table 8, show the NAHV/ILT 295-149 vaccine protected better against virulent Marek's disease challenge, than the commercial vaccine.

TABLE 8

Efficacy of the NAHV/ILT 295-149 Recombinant Vaccine Against Virulent Marek's Disease Virus Challenge

| Group | Route | Dose[a] | Challenge[b] | Protection Ratio[c] | % Protected |
|---|---|---|---|---|---|
| Non-vac. | — | — | — | 33/33 | — |
| Non-vac. | — | — | RB1B | 2/35 | 6% |
| NAHV/ILT 295-149 | in ovo | 1500 pfu | RB1B | 25/26 | 96% |
| NAHV/ILT 295-149 | SC | 1500 pfu | RB1B | 32/34 | 94% |
| Rispens | SC | As per label | RB1B | 26/33 | 79% |

[a]In ovo dose: PFU/0.05 ml; SC dose: PFU/0.2 ml.
[b]Challenge 5 days post-vaccination, intra-abdominal Although certain presently preferred embodiments of the invention have been disclosed herein, it will be apparent to those skilled in the art to which the invention pertains that variation and modification of described embodiments may be made without departing from the spirit and scope of the invention. Accordingly, it is intended that the invention be limited to the extent required by the appended claims and the applicable rules of law.

What is claimed is:

1. A method of making a recombinant chimeric virus (NAHV 295-01) having the ATCC No. PTA-3451, comprising cotransfecting overlapping subgenomic fragments in chicken embryo fibroblast cells employing the following subgenomic clones and enzymes:
   (i) 989-72.8#1 with I-SceI;
   (ii) 407-32.2C3 with NotI;
   (iii) 172-07.BA2 with BamHI;
   (iv) 407-32.5G6 with NotI; and
   (v) 407-32.1C1 with NotI.

2. A method of making a recombinant chimeric virus (NAHV/NDV 295-93) having the ATCC No. PTA-3453, comprising cotransfecting overlapping subgenomic fragments in chicken embryo fibroblast cells employing the following subgenomic clones and enzymes:
   (i) 1002-75.4 with I-SceI;
   (ii) 407-32.2C3 with NotI;

(iii) 172-07.BA2 with BamHI;
(iv) 407-32.5G6 with NotI; and
(v) 407-32.1C1 with NotI.

3. A method of making a recombinant chimeric virus (NAHV/ILT 295-149) having the ATCC No. PTA-3452, comprising cotransfecting overlapping subgenomic fragments in chicken embryo fibroblast cells employing the following subgenomic clones and enzymes:

(i) 1012-89.2 with I-SceI;
(ii) 407-32.2C3 with NotI;
(iii) 172-07.BA2 with BamHI;
(iv) 407-32.5G6 with NotI; and
(v) 407-32.1C1 with NotI.

* * * * *